US011673958B2

(12) United States Patent
Hansen et al.

(10) Patent No.: US 11,673,958 B2
(45) Date of Patent: Jun. 13, 2023

(54) GLYCOSYLATED ANTIBODIES

(71) Applicant: Hoffmann-La Roche Inc., Nutley, NJ (US)

(72) Inventors: Silke Hansen, Iffeldorf (DE); Klaus-Peter Kuenkele, Benediktbeuern (DE); Dietmar Reusch, Munich (DE); Ralf Schumacher, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/195,066

(22) Filed: Mar. 3, 2014

(65) Prior Publication Data

US 2014/0193404 A1    Jul. 10, 2014

Related U.S. Application Data

(60) Continuation of application No. 13/298,553, filed on Nov. 17, 2011, now Pat. No. 8,703,919, which is a continuation of application No. 12/873,658, filed on Sep. 1, 2010, now abandoned, which is a division of application No. 11/732,974, filed on Apr. 5, 2007, now Pat. No. 7,846,724.

(30) Foreign Application Priority Data

Apr. 11, 2006  (EP) .................... 06007565
Aug. 3, 2006   (EP) .................... 06016203

(51) Int. Cl.
*C07K 16/00*   (2006.01)
*C07K 16/28*   (2006.01)

(52) U.S. Cl.
CPC .......... *C07K 16/2863* (2013.01); *C07K 16/00* (2013.01); *C07K 2317/41* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 5,202,238 A | 4/1993 | Fell et al. | |
| 5,204,244 A | 4/1993 | Fell et al. | |
| 5,610,297 A | 3/1997 | Powers | |
| 5,770,429 A | 6/1998 | Lonberg et al. | |
| 7,432,359 B2 | 10/2008 | Kataoka et al. | |
| 7,612,178 B2 | 11/2009 | Hariharan et al. | |
| 2003/0165502 A1 | 9/2003 | Fujita-Yamaguchi | |
| 2004/0018191 A1 | 1/2004 | Wang et al. | |
| 2004/0241817 A1 | 12/2004 | Umana et al. | |
| 2005/0084906 A1 | 4/2005 | Goetsch et al. | |
| 2005/0249730 A1 | 11/2005 | Goetsch et al. | |
| 2007/0015239 A1 | 1/2007 | Bihoreau et al. | |
| 2007/0122404 A1 | 5/2007 | O'Keefe | |
| 2008/0014203 A1 | 1/2008 | Hansen et al. | |

FOREIGN PATENT DOCUMENTS

| | | |
|---|---|---|
| EP | 1176195 | 1/2002 |
| WO | WO 87/05330 | 9/1987 |
| WO | WO 94/11026 | 5/1994 |
| WO | WO 95/14930 | 6/1995 |
| WO | WO 98/22136 | 5/1998 |
| WO | WO 99/51642 | 10/1999 |
| WO | WO 99/54342 | 10/1999 |
| WO | WO 00/61739 | 10/2000 |
| WO | WO 00/61739 A1 | 10/2000 |
| WO | WO 01/14424 | 3/2001 |
| WO | WO 02/053596 | 7/2002 |
| WO | WO 03/059951 | 7/2003 |
| WO | WO 03/100008 | 12/2003 |
| WO | WO 03/106621 | 12/2003 |
| WO | WO 2004/071529 | 8/2004 |
| WO | WO 2004/083248 | 9/2004 |
| WO | WO 2004/087756 | 10/2004 |
| WO | WO 2005/005635 | 1/2005 |
| WO | WO 2005/016967 | 2/2005 |
| WO | WO 2005/016970 | 2/2005 |
| WO | WO 2005/023872 | 3/2005 |
| WO | WO 2005/040221 | 5/2005 |
| WO | WO 2005/040221 A1 | 5/2005 |
| WO | WO 2005/058967 | 6/2005 |
| WO | WO 2005/082415 | 9/2005 |
| WO | WO 2005/094376 | 10/2005 |
| WO | WO 2005/115453 | 12/2005 |
| WO | WO 2006/008639 | 1/2006 |
| WO | WO 2006/013472 | 2/2006 |
| WO | WO 2007/048077 A2 | 4/2007 |
| WO | WO 2007/115814 | 10/2007 |
| WO | WO 2014/172371 A2 | 10/2014 |

OTHER PUBLICATIONS

D38, Matsumiya et al., J. Mol. Biol. 368 (2007) 767-779.
Novartis AG, Written submission against EP 2007809, Apr. 14, 2015.
D39, Shatz et al., mAbs 5 (2013) 872-881.
Summons to attent oral proceedings pursuant to Rule 115(1) EPC, mailed on Oct. 14, 2014, issued by the EPO.
D41, Tu et al., mAbs 4 (2012) 475-487.
Declarations of Dr. Patel, Dr. Schuessler and Dr. Aich, in the matter of opposition to EP 2007809, Apr. 16, 2015.
D36, M.J. Corbley, 'Protein Therapeutics in Oncology,' Chapter 7, p. 138, in 'Signaling Pathways in Cancer Pathogenesis and Therapy,' David A. Frank (ed.), Springer, 2012.

(Continued)

*Primary Examiner* — Michail A Belyavskyi
(74) *Attorney, Agent, or Firm* — Baker Botts L.L.P.

(57) ABSTRACT

The invention provides an antibody comprising human IgG1 or IgG3 heavy chain constant domains that are glycosylated with a sugar chain at Asn297, said antibody being characterized in that the amount of fucose within said sugar chain is at least 99%, and in addition the amount of NGNA is 1% or less and/or the amount of N-terminal alpha 1,3 galactose is 1% or less, and uses thereof.

18 Claims, 1 Drawing Sheet

(56) References Cited

OTHER PUBLICATIONS

Glaxo Group Ltd., Opponent 2's R116 Submission Before Oral Proceedings, Apr. 16, 2015.
Wuhrer M. (2013), Glycoconj J. 30, pp. 11-22.
D42, Shah et al., J. Am. Soc. Mass Spectrom 25 (2014) 999-1011.
D35, D. J. King, 'Applications and Engineering of Monoclonal Antibodies,' CRC Press (1998), pp. 54-55.
Adams et al., "Structure and function of the type 1 insulin-like growth factor receptor," Cell. Mol. Life Sci. 57(7):1050-1093 (2000).
Beck et al., "Characterization by liquid chromatography combined with mass spectrometry of monoclonal anti-IGF-1 receptor antibodies produced in CHO and NS0 cells," J. Chromatogr. B Analyt. Technol. Biomed, Life Sci. 819(2):203-218 (2005).
Benini et al., "Inhibition of insulin-like growth factor I receptor increases the antitumor activity of doxorubicin and vincristine against Ewing's sarcoma cells," Clin. Cancer Res. 7(6):1790-1797 (2001).
Bergmann et al., "Insulin-like growth factor I overexpression in human pancreatic cancer: evidence for autocrine and paracrine roles," Cancer Res. 55(10):2007-2011 (1995).
Bergwerff et al., "Variation in N-linked carbohydrate chains in different batches of two chimeric monoclonal IgG1 antibodies produced by different murine SP2/0 transfectoma cell subclones," Glycoconj. J. 12(3):318-330 (1995).
Boerner et al., "Production of antigen-specific human monoclonal antibodies from in vitro-primed human splenocytes," J. Immunol. 147(1):86-95 (1991).
Bowie et al., "Deciphering the message in protein sequence: tolerance to amino acid substitutions," Science 247(4948):1306-1310 (1990).
Brüggemann et al., "Comparison of the effector functions of human immunoglobulins using a matched set of chimeric antibodies," J. Exp. Med. 166(5):1351-1361 (1987).
Brüggemann et al., "Designer mice: the production of human antibody repertoires in transgenic animals," Year Immunol. 7:33-40 (1993).
Brunetti et al., "Monoclonal antibodies to the human insulin receptor mimic a spectrum of biological effects in transfected 3T3/HIR fibroblasts without activating receptor kinase," Biochem. Biophys. Res. Commun. 165(1):212-218 (1989).
Calculation using data from D13 reference listed in Glaxo opposition (D13 reference, BERGWERFF, "Variation in N-linked carbohydrate chains in different batches of two chimeric monoclonal IgG1 antibodies produced by different murine SP2/0 transfectoma cell subclones," Glycoconj. J. 12(3):318-330 (1995).
Chen et al., "B cell development in mice that lack one or both immunoglobulin kappa light chain genes," EMBO J. 12(3):821-830 (1993).
Chung et al., "Quantitative evaluation of fucose reducing effects in a humanized antibody on Fcγ receptor binding and antibody-dependent cell-mediated cytotoxicity activities," MAbs 4(3):326-40 (2012) (Epub Apr. 26, 2012).
Chusainow et al., "A study of monoclonal antibody-producing CHO cell lines: what makes a stable high producer?" Biotechnol. Bioeng. 102(4):1182-1196 (2009).
Cole, S. P. C., D. Kozbor, and J. C. Roder. "The EBV-hybridoma technique and its application to human lung cancer." Monoclonal Antibodies and Cancer Therapy 27 (1985): 77-96.
Davies et al., "Expression of GnTIII in a recombinant anti-CD20 CHO production cell line: Expression of antibodies with altered glycoforms leads to an increase in ADCC through higher affinity for FC gamma RIII," Biotechnol. Bioeng. Aug. 20, 2001;74(4):288-294 (. 288-294).
Decision of the Opposition Division for European Patent Appication No. 07724105.7 dated Jul. 13, 2015.
Delafontaine et al., "Epitope mapping of the alpha-chain of the insulin-like growth factor I receptor using antipeptide antibodies," J. Mol. Cell. Cardiol. 26(12):1659-1673 (1994).
Derouazi et al., "Genetic characterization of CHO production host DG44 and derivative recombinant cell lines," Biochem. Biophys. Res. Commun. 340(4):1069-1077 (2006) (Epub Dec. 27, 2005).
Dricu et al., "Expression of the insulin-like growth factor 1 receptor (IGF-1R) in breast cancer cells: evidence for a regulatory role of dolichyl phosphate in the transition from an intracellular to an extracellular IGF-1 pathway," Glycobiology 9(6):571-579 (1999).
Fishwild et al., "High-avidity human IgG kappa monoclonal antibodies from a novel strain of minilocus transgenic mice," Nat. Biotechnol. 14(7):845-851 (1996).
Flintoff et al., "Isolation and partial characterization of three methotrexate-resistant phenotypes from Chinese hamster ovary cells," Somatic Cell Genet. 2(3):245-261 (1976).
Flintoff et al., "Overproduction of dihydrofolate reductase and gene amplification in methotrexate-resistant Chinese hamster ovary cells," Mol. Cell. Biol. 2(3):275-285 (1982).
Forsayeth et al., "Monoclonal antibodies to the human insulin receptor that activate glucose transport but not insulin receptor kinase activity," Proc. Natl. Acad. Sci. U.S.A. 84(10):3448-3451 (1987).
Fujii, "Structural heterogeneity of sugar chains in immunoglobulin G. Conformation of immunoglobulin G molecule and substrate specificities of glycosyltransferases," J. Biol. Chem. 265(11):6009-6018 (1990).
Gandor et al., "Amplification and expression of recombinant genes in serum-independent Chinese hamster ovary cells," FEBS Lett. 377(3):290-294 (1995).
Gustafson et al., "The cysteine-rich domains of the insulin and insulin-like growth factor I receptors are primary determinants of hormone binding specificity. Evidence from receptor chimeras," J. Biol. Chem. 265(30):18663-186637 (1990).
Hailey et al., "Neutralizing anti-insulin-like growth factor receptor 1 antibodies inhibit receptor function and induce receptor degradation in tumor cells," Mol. Cancer Ther. 1(14):1349-1353 (2002).
Hoogenboom et al., "By-passing immunisation. Human antibodies from synthetic repertoires of germline VH gene segments rearranged in vitro," J. Mol. Biol. 227(2):381-388 (1992).
Hossler et al., "Optimal and consistent protein glycosylation in mammalian cell culture," Glycobiology 19(9):936-949 (Epub Jun. 3, 2009).
Hoyne et al., "Properties of an insulin receptor with an IGF-1 receptor loop exchange in the cysteine-rich region," FEBS Lett. 469(1):57-60 (2000).
Huang et al., "Impact of variable domain glycosylation on antibody clearance: an LC/MS characterization," Anal. Biochem. 349(2):197-207 (2006) (Epub Nov. 28, 2005).
Ito et al., "Recognition of N-glycolylneuraminic acid linked to galactose by the alpha2,3 linkage is associated with intestinal replication of influenza A virus in ducks," J. Virol. 74(19):9300-9305 (2000).
Jakobovits et al., "Germ-line transmission and expression of a human-derived yeast artificial chromosome," Nature 362(6417):255-258 (1993).
Jakovovits et al., "Analysis of homozygous mutant chimeric mice: deletion of the immunoglobulin heavy-chain joining region blocks B-cell development and antibody production," Proc. Natl. Acad. Sci. U.S.A. 90(6):2551-2555 (1993).
Jefferis et al., "IgG-Fc-mediated effector functions: molecular definition of interaction sites for effector ligands and the role of glycosylation," Immunol. Rev. 163:59-76 (1998).
Jefferis, "Glycosylation of recombinant antibody therapeutics," Biotechnol. Prog. 21(1):11-16 (2005).
Jenkins et al., "Getting the glycosylation right: implications for the biotechnology industry," Nat. Biotechnol. 14(8):975-981 (1996).
Johnson et al., "Kabat database and its applications: 30 years after the first variability plot," Nucleic Acids Res. 28(1):214-218 (2000).
Kalebic et al., "In vivo treatment with antibody against IGF-1 receptor suppresses growth of human rhabdomyosarcoma and down-regulates p34cdc2," Cancer Res. 54(21):5531-5534 (1994).
Kane et al., "A new vector using the human multidrug resistance gene as a selectable marker enables overexpression of foreign genes in eukaryotic cells," Gene 84(2):439-446 (1989).

(56) References Cited

OTHER PUBLICATIONS

Kanter-Lewensohn et al., "Expression of the insulin-like growth factor-1 receptor and its anti-apoptotic effect in malignant melanoma: a potential therapeutic target," Melanoma Res. 8(5):389-397 (1998).
Kato et al., "Role of tyrosine kinase activity in signal transduction by the insulin-like growth factor-I (IGF-I) receptor. Characterization of kinase-deficient IGF-I receptors and the action of an IGF-I-mimetic antibody (alpha IR-3)," J. Biol. Chem. Feb. 5, 1993;268(4):2655-2661 (1993).
Kolhekar et al., "Peptidylglycine alpha-hydroxylating monooxygenase: active site residues, disulfide linkages, and a two-domain model of the catalytic core," Biochemistry 36(36):10901-10909 (1997).
Kull et al., "Monoclonal antibodies to receptors for insulin and somatomedin-C," J. Biol. Chem. 258(10):6561-6566 (1983).
Kunkel et al., "Comparisons of the glycosylation of a monoclonal antibody produced under nominally identical cell culture conditions in two different bioreactors," Biotechnol. Prog. 16(3):462-470 (2000).
Kunkel et al., "Dissolved oxygen concentration in serum-free continuous culture affects N-linked glycosylation of a monoclonal antibody," J. Biotechnol. 62(1):55-71 (1998).
Lammers et al., "Differential signalling potential of insulin- and IGF-1-receptor cytoplasmic domains," EMBO J. 8(5):1369-1375 (1989).
Li et al., "Single-chain antibodies against human insulin-like growth factor I receptor: expression, purification, and effect on tumor growth," Cancer Immunol. Immunother. 49(4-5):243-252 (2000).
Li et al., "Two new monoclonal antibodies against the alpha subunit of the human insulin-like growth factor-I receptor," Biochem. Biophys. Res. Commun. 196(1):92-98 (1993).
Lifely et al., "Glycosylation and biological activity of CAMPATH-1H expressed in different cell lines and grown under different culture conditions," Glycobiology 5(8):813-822 (1995).
Lonberg et al., "Antigen-specific human antibodies from mice comprising four distinct genetic modifications," Nature 368(6474):856-859 (1994).
Love et al., "Recombinant antibodies possessing novel effector functions," Methods Enzymol. 178:515-527 (1989).
Lubeck et al., "The interaction of murine IgG subclass proteins with human monocyte Fc receptors," J. Immunol.135(2):1299-1304 (1985).
Lund et al., "Control of IgG/Fc glycosylation: a comparison of oligosaccharides from chimeric human/mouse and mouse subclass immunoglobulin Gs," Mol. Immunol. 30(8):741-748 (1993).
Ma et al., "Carbohydrate analysis of a chimeric recombinant monoclonal antibody by capillary electrophoresis with laser-induced fluorescence detection," Anal. Chem. 71(22):5185-5192 (1999).
Makrides, "Components of vectors for gene transfer and expression in mammalian cells," Protein Expr. Purif. 17(2):183-202 (1999).
Marked Antibodies, data taken from STADLMANN, "Analysis of immunoglobulin glycosylation by LC-ESI-MS of glycopeptides and oligosaccharides," Proteomics 8(14):2858-2871 (2008); vol. 10 pp. 477-486 (2007).
Marks et al., "By-passing immunization. Human antibodies from V-gene libraries displayed on phage," J. Mol. Biol. 222(3):581-597 (1991).
Mimura et al., "Butyrate increases production of human chimeric IgG in CHO-K1 cells whilst maintaining function and glycoform profile," J. Immunol. Methods. 247(1-2):205-216 (2001).
Mizouchi et al., "Structural and numerical variations of the carbohydrate moiety of immunoglobulin G," J. Immunol. 129(5):2016-2020 (1982).
Morgan et al., "Mapping surface structures of the human insulin receptor with monoclonal antibodies: localization of main immunogenic regions to the receptor kinase domain," Biochemistry 25(6):1364-1371 (1986).
Mori et al., "Engineering Chinese hamster ovary cells to maximize effector function of produced antibodies using FUT8 siRNA," Biotechnol. Bioeng. 88(7):901-908 (2004).
Morrison et al., "Chimeric human antibody molecules: mouse antigen-binding domains with human constant region domains," Proc. Natl. Acad. Sci. U.S.A. 81(21):6851-6855 (1984).
Müthing et al., "Effects of buffering conditions and culture pH on production rates and glycosylation of clinical phase I anti-melanoma mouse IgG3 monoclonal antibody R24," Biotechnol. Bioeng. 83(3):321-334 (2003).
Nahrgang et al., "Products from Cells, Cells as Products," Animal Cell Technology:259-261 (1999).
Neuberger et al., "A hapten-specific chimaeric IgE antibody with human physiologic effector function," Nature 314(6008):268-270 (1985).
Niwa et al., "Defucosylated chimeric anti-CC chemokine receptor 4 IgG1 with enhanced antibody-dependent cellular cytotoxicity shows potent therapeutic activity to T-cell leukemia and lymphoma," Cancer Res. 64(6):2127-2133 (2004).
Niwa et al., "Enhanced natural killer cell binding and activation by low-fucose IgG1 antibody results in potent antibody-dependent cellular cytotoxicity induction at lower antigen density," Clin. Cancer Res. 11(6):2327-2336 (2005).
Niwa et al., "Enhancement of the antibody-dependent cellular cytotoxicity of low-fucose IgG1 Is independent of FcgammaRIIIa functional polymorphism," Clin. Cancer Res. 10(18 Pt 1):6248-6255 (2004).
Niwa et al., "IgG subclass-independent improvement of antibody-dependent cellular cytotoxicity by fucose removal from Asn297-linked oligosaccharides," J. Immunol. Methods 306(1-2):151-160 (2005) (Epub Sep. 22, 2005).
Notice of opposition (Glaxo Group Ltd.) by the European Patent Office, issued on Jun. 18, 2013, in the co-pending European Patent Publication No. EP 2007809.
Notice of opposition (Novartis AG) by the European Patent Office, issued on Jun. 18, 2013, in the co-pending European Patent Publication No. EP 2007809.
O'Brien et al., "Monoclonal antibodies to the insulin receptor stimulate the intrinsic tyrosine kinase activity by cross-linking receptor molecules," EMBO J. 6(13):4003-4010 (1987).
Pallavicini et al., "Effects of methotrexate on transfected DNA stability in mammalian cells," Mol. Cell. Biol. 10(1):401-404 (1990).
Patel et al., "Different culture methods lead to differences in glycosylation of a murine IgG monoclonal antibody," Biochem J. 285 ( Pt 3):839-845 (1992).
Pessino et al., "Antipeptide antibodies toward the extracellular domain of insulin receptor beta-subunit," Biochem. Biophys. Res. Commun. 162(3):1236-1243 (1989).
Pietrzkowski et al., "Constitutive expression of insulin-like growth factor 1 and insulin-like growth factor 1 receptor abrogates all requirements for exogenous growth factors," Cell Growth Differ. 3(4):199-205 (1992).
Prigent et al., "Identification of epitopes on the human insulin receptor reacting with rabbit polyclonal antisera and mouse monoclonal antibodies," J. Biol. Chem. 265(17):9970-9977 (1990).
Raju et al., "Species-specific variation in glycosylation of IgG: evidence for the species-specific sialylation and branch-specific galactosylation and importance for engineering recombinant glycoprotein therapeutics," Glycobiology 10(5):477-486 (2000).
Raju, BioProcess International 1:44-53 (2003).
Reichmann et al., "Reshaping human antibodies for therapy," Nature 332(6162):323-327 (1988).
Rohlik et al., "An antibody to the receptor for insulin-like growth factor I inhibits the growth of MCF-7 cells in tissue culture," Biochem. Biophys. Res. Commun. 149(1):276-281 (1987).
Routier et al., "Quantitation of the oligosaccharides of human serum IgG from patients with rheumatoid arthritis: a critical evaluation of different methods," J. Immunol. Methods. 213(2):113-130 (1998).
Routier et al., "The glycosylation pattern of humanized IgGI antibody (D1.3) expressed in CHO cells," Glycoconj. J. 14(2):201-207 (1997).
Sandoglobulin Product Profile 1997.

(56) References Cited

OTHER PUBLICATIONS

Schaefer et al., "Deletion analysis of the human insulin receptor ectodomain reveals independently folded soluble subdomains and insulin binding by a monomeric alpha-subunit," J. Biol. Chem. 265(22):13248-13253 (1990).

Schlaeger et al., "Transient gene expression in mammalian cells grown in serum-free suspension culture," Cytotechnology 30(1-3):71-83 (1999).

Schnitzer et al., European Journal of Cancer (XP005810433), 4(12) 2006.

Scotlandi et al., "Effectiveness of insulin-like growth factor I receptor antisense strategy against Ewing's sarcoma cells," Cancer Gene Ther. 9(3):296-307 (2002).

Scotlandi et al., "Expression of an IGF-I receptor dominant negative mutant induces apoptosis, inhibits tumorigenesis and enhances chemosensitivity in Ewing's sarcoma cells," Int. J. Cancer 101(1):11-16 (2002).

Sheeley et al., "Characterization of monoclonal antibody glycosylation: comparison of expression systems and identification of terminal alpha-linked galactose," Anal. Biochem. 247(1):102-110 (1997).

Shields et al., "Lack of fucose on human IgG1 N-linked oligosaccharide improves binding to human Fcgamma RIII and antibody-dependent cellular toxicity," J. Biol. Chem. 277(30):26733-26740. (Epub May 1, 2002).

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem. 278(5):3466-3473 (2003) (Epub Nov. 8, 2002).

Soos et al., "Monoclonal antibodies to the insulin receptor mimic metabolic effects of insulin but do not stimulate receptor autophosphorylation in transfected NIH 3T3 fibroblasts," Proc. Natl. Acad. Sci. U.S.A. 86(14):5217-5221 (1989).

Stabila et al., "Cell surface expression of a human IgG Fc chimera activates macrophages through Fc receptors," Nat. Biotechnol. 16(13):1357-1360 (1998).

Stadlmann, "Analysis of immunoglobulin glycosylation by LC-ESI-MS of glycopeptides and oligosaccharides," Proteomics 8(14):2858-2871 (2008).

Stella, V. J., and Himmelstein, K. J. (1985). Prodrugs: a chemical approach to targeted drug delivery. In Directed Drug Delivery (pp. 247-267). Humana Press.

Surinya et al., "Role of insulin receptor dimerization domains in ligand binding, cooperativity, and modulation by anti-receptor antibodies," J. Biol. Chem. 277(19):16718-16725 (2002) (Epub Mar. 1, 2002).

Taylor et al., "Insulin-like and insulin-inhibitory effects of monoclonal antibodies for different epitopes on the human insulin receptor," Biochem. J. 242(1):123-129 (1987).

Thelander et al., "Molecular cloning and expression of the functional gene encoding the M2 subunit of mouse ribonucleotide reductase: a new dominant marker gene," EMBO J. 8(9):2475-2479 (1989).

Tulloch et al., "Single-molecule imaging of human insulin receptor ectodomain and its Fab complexes," J. Struct. Biol. 125(1):11-18 (1999).

Urlaub et al., "Deletion of the diploid dihydrofolate reductase locus from cultured mammalian cells," Cell 33(2):405-412 (1983).

Urlaub et al., "Effect of gamma rays at the dihydrofolate reductase locus: deletions and inversions," Somat. Cell. Mol. Genet. 12(6):555-566 (1986).

Van Dijk et al., "Human antibodies as next generation therapeutics," Curr. Opin. Chem. Biol. 5(4):368-374 (2001).

Wagner-Rousset et al., "The way forward, enhanced characterization of therapeutic antibody glycosylation: comparison of three level mass spectrometry-based strategies," J. Chromatogr. B Analyt. Technol. Biomed. Life Sci. 872(1-2):23-37 (2008) (Epub Apr. 15, 2008).

Werner et al., "Appropriate mammalian expression systems for biophar-maceuticals," Drug Res. 48:870-880 (1998).

Wilman, D. E. V., Prodrugs in Cancer Chemotherapy Biochemical Society Transactions, 615$^{th}$ Meeting, Belfast, Ireland, pp. 375-383 (1986).

Wright et al., "Effect of glycosylation on antibody function: implications for genetic engineering," Trends Biotechnol. 15(1):26-32 (1997).

Wurm et al., "Inducible overproduction of the mouse c-myc protein in mammalian cells," Proc. Natl. Acad. Sci. U.S.A. 83(15):5414-5418 (1986).

Wurm, "Production of recombinant protein therapeutics in cultivated mammalian cells," Nat. Biotechnol. 22(11):1393-1398 (2004).

Zhu et al., "Production of human monoclonal antibody in eggs of chimeric chickens," Nat. Biotechnol. 23(9):1159-1169 (2005) (Epub Aug. 28, 2005).

Dall'Ozzo et al., 2004, "Rituximab-dependent cytotoxicity by natural killer cells: influence of FCGR3A polymorphism on the concentration-effect relationship," Cancer Res. 64(13): 4664-4669.

Dashivets et al., 2015, "Multi-angle effector function analysis of human monoclonal IgG glycovariants," PLoS One. 10(12):e0143520.

Golay et al., 2013, "Glycoengineered CD20 antibody obinutuzumab activates neutrophils and mediates phagocytosis through CD16B more efficiently than rituximab," Blood. 122(20): 3482-3491.

Hogarth et al., 2012, "Fc receptor-targeted therapies for the treatment of inflammation, cancer and beyond," Nat Rev Drug Discov. 11(4): 311-331.

Okazaki et al., 2004, "Fucose depletion from human IgG1 oligosaccharide enhances binding enthalpy and association rate between IgG1 and FcgammaRIIIa," J Mol Biol. 336(5): 1239-1249.

F. Hoffmann La Roche AG, Response to Article 121 EPC, filed Nov. 25, 2009, in European Patent Application No. 07 724 105.7-2401 (3 pages).

F. Hoffmann La Roche AG, Corrected Enclosure 2 to letter of Jun. 14, 2010, in European Patent Application No. 07 724 105.7-2401 (1 page).

Novartis AG, Statement of Grounds of Opposition to European Patent Publication No. EP 2 007 809 B1, filed Jun. 12, 2013 (9 pages).

Glaxo Group Limited, Statement of Grounds of Opposition to European Patent Publication No. EP 2 007 809 B1, filed Jun. 12, 2013 (23 pages).

Declaration of Dietmar Reusch, dated Jan. 15, 2014, in the Matter of Opposition to European Patent Publication No. EP 2 007 809 B1 (16 pages; incl. Exhibits 3-9).

Declaration of Silke Hansen, dated Jan. 20, 2014, in the Matter of Opposition to European Patent Publication No. EP 2 007 809 B1 (3 pages).

F. Hoffmann-La Roche AG, Observations on Oppositions, filed Jan. 20, 2014, in the Matter of Opposition to European Patent Publication No. EP 2 007 809 B1 (24 pages).

European Patent Office, Preliminary Opinion dated Oct. 14, 2014, in the Matter of Opposition to European Patent Publication No. EP 2 007 809 B1 (15 pages).

Novartis AG, Written Submissions filed Apr. 14, 2015, in the Matter of Opposition to European Patent Publication No. EP 2 007 809 B1 (12 pages).

Glaxo Group Limited, Written Submissions filed Apr. 16, 2015, in the Matter of Opposition to European Patent Publication No. EP 2 007 809 B1 (23 pages).

Declaration of Dietmar Reusch, dated Jun. 2, 2015, in the Matter of Opposition to European Patent Publication No. EP 2 007 809 B1 (9 pages; incl. Exhibit 1).

F. Hoffmann-La Roche AG, Response to Written Submissions filed Jun. 5, 2015, in the Matter of Opposition to European Patent Publication No. EP 2 007 809 B1 (23 pages).

European Patent Office, Interlocutory Decision dated Jul. 13, 2015, in the Matter of Opposition to European Patent No. EP 2 007 809 B1 (16 pages).

Glaxo Group Limited, Grounds of Appeal, filed Nov. 13, 2015, in the Matter of Opposition to European Patent No. EP 2 007 809 B1 (24 pages).

Declaration of Tomas Rejtar, dated Nov. 20, 2015, in the Matter of Opposition to European Patent Publication EP 2 007 809 B1 (4 pages).

(56) References Cited

OTHER PUBLICATIONS

Novartis AG, Grounds of Appeal, filed Nov. 23, 2015, in the Matter of Opposition to European Patent Publication No. EP 2 007 809 B1 (23 pages).
Declaration of Tilman Schlothauer, dated Apr. 7, 2016, in the Matter of Opposition to European Patent Publication No. EP 2 007 809 B1 (11 pages; incl. Exhibit 7).
Declaration of Dietmar Reusch & Markus Haberger, dated Apr. 7, 2016, in the Matter of Opposition to European Patent Publication No. EP 2 007 809 B1 (9 pages; incl. Exhibit 3).
F. Hoffmann-La Roche AG, Observations on Grounds of Appeal, filed Apr. 7, 2016, in the Matter of Opposition to European Patent Publication No. EP 2 007 809 B1 (58 pages).
English Translation of the Action for Infringement by F. Hoffmann-La Roche AG dated Sep. 27, 2016 (23 pages).
EPO Appeal T1784/15-3.3.04, Opposition against EP 2 007 809, D48: Declaration of Dr. Kurt Forrer dated Aug. 23, 2016 (57 pages).
EPO Appeal T1784/15-3.3.04, Opposition against EP 2 007 809, D49: Declaration of Dr. Nicolas Naula dated Aug. 24, 2016 (3 pages).
EPO Appeal T1784/15-3.3.04, Opposition against EP 2 007 809, D50: Evidence of sale in Italy in 2005 showing details of the shipments of the sold Simulect products to the Italian customers (hospitals) submitted by Opponent Novartis AG on Aug. 25, 2016 to EPO (1 page).
EPO Appeal T1784/15-3.3.04, Opposition against EP 2 007 809, D51: DrugBank: Basiliximab (http://www.drugbank.ca/drugs/DB00074) (11 pages).
EPO Appeal T1784/15-3.3.04, Opposition against EP 2 007 809, D53: EMA product information on Simulect (44 pages) Annex I—Summary of Product Characteristics; Annex II—Manufacturers of the Biological Active Substance and Manufacturing Authorization Holder Responsible for Batch Release; Conditions of the Marketing Authorisation; Annex III—Labelling and Package Leaflet.
Epo Appeal T1784/15-3.3.04, Opposition against EP 2 007 809, D54: Vezer et al., "Authorized manufacturing changes for therapeutic monoclonal antibodies (mAbs) in European Public Assessment Report (EPAR) documents", Curr Med Res Opin., 32(5):829-834 (2016).
EPO Appeal T1784/15-3.3.04, Opposition against EP 2 007 809, Package Leaflet: Information for the user—Ilaris 150 mg powder for solution for injection Canakinumab, submitted by Opponent Novartis to EPO on Nov. 4, 2016 (12 pages).
EPO Appeal T1784/15-3.3.04, Opposition against EP 2 007 809, submission of Opponent Novartis to EPO dated Aug. 25, 2016 (8 pages).
EPO Appeal T1784/15-3.3.04, Opposition against EP 2 007 809, submission of Patentee F. Hoffmann-La Roche to EPO dated Dec. 2, 2016 (19 pages).
Opposition against EP 2 007 809, EPO Communication dated Jul. 8, 2013 regarding Notices of Opposition (R. 79(1) EPC) (1 page).
Opposition against EP 2 007 809, Patentee F. Hoffmann-La Roche Observations on Opposition filed Jan. 20, 2014 (77 pages) including: Auxiliary Request; D31: Roche response in European Patent Application No. 07724105.7-2401 dated Nov. 23, 2009; D32: Declaration of Mr. Dietmar Reusch (including Exhibits 1-9): Ex. 1—CV of Dietmar Reusch, Ex. 2—List of Cited Documents, Ex. 3—D5—Figure 2., Ex. 4—D24—Enlarged Part of Figure 2, Ex. 5—Excerpt from Table 1 of D25 with comments on deviations from the results shown in Figure 4B, Ex. 6—D25—Enlarged Part of Figure 4, Ex. 7—D28—Enlarged Part of Figure 1B., Ex. 8—D29—Enlarged Part of Figure 7C, Ex. 9—D29—Enlarged Part of Figure 7A; D33: Declaration of Dr. Silke Hansen (including Exhibit 1): Ex. 1—CV of Silke Hansen, PhD; D34: Corrected Enclosure 2 to letter of Jun. 14, 2010 in European Patent Application No. 07724105.7-2401—Experimental Report; D35: King, "Applications and Engineering of Monoclonal Antibodies", CRC Press, 54-55 (1998); D36: Corbley, "Protein Therapeutics in Oncology", Chapter 8, p. 138 in "Signaling Rathways in Cancer Pathogenesis and Therapy", David A. Frank (ed.), Springer (2012); D37: Wuhrer, "Glycomics using mass spectrometry", Glycoconj J., 30(1):11-22 (2013); Consolidated list of cited documents.
Opposition against EP 2 007 809, Patentee F. Hoffmann-La Roche Written Submission in Preparation of the Oral Proceedings, filed Apr. 14, 2015 (2 pages).
Opposition against EP 2 007 809, Opponent Glaxo Group Limited's R116 Submissions Before Oral Proceedings filed Apr. 16, 2015 (90 pages) including: D38: MATSUMIYA et al., "Structural comparison of fucosylated and nonfucosylated Fc fragments of human immunoglobulin G1", J Mol Biol., 368(3):767-779 (2007); D39: Shatz et al., "Knobs-into-holes antibody production in mammalian cell lines reveals that asymmetric afucosylation is sufficient for full antibody-dependent cellular cytotoxicity", MAbs, 5(6):872-881 (2013); D40: Declaration of Mr. Mitul Patel, Dr. Hillary Schuessler and Udayanath Aich (including Exhibits A-C): Ex. A—CV of Mitul Patel, Ex. B—CV of Hillary A. Schuessler, Ex. C—CV of Dr. Udayanath Aich; D41: Yu et al., "Production, characterization, and pharmacokinetic properties of antibodies with N-linked mannose-5 glycans", MAbs, 4(4):475-487 (2012); D42: Shah et al., "LC-MS/MS peptide mapping with automated data processing for routine profiling of N-glycans in immunoglobulins", J Am Soc Mass Spectrom, 25(6):999-1011 (2014).
Opposition against EP 2 007 809, Patentee F. Hoffmann-La Roche Response to Written Submissions filed by Opponents Novartis AG and Glaxo Group Limited, filed Jun. 5, 2015 (66 pages) including: New Auxiliary Requests I to VI (clean copy and marked-up copy); D43: Declaration of Dietmar Reusch (including Exhibit 1): Ex. 1—Enlarged Figure 8 of 25; D44: NIWA et al., "Defucosylated chimeric anti-CC chemokine receptor 4 IgG1 with enhanced antibody-dependent cellular cytotoxicity shows potent therapeutic activity to T-cell leukemia and lymphoma", Cancer Res., 64(6):2127-2133 (2004); and Consolidated list of cited documents.
Opposition against EP 2 007 809, EPO Communication Regarding Interlocutory Decision in Opposition Proceedings (Art. 101(3)(a) and 106(2) EPC) dated Jul. 13, 2015 (55 pages) including: The Grounds for the decision (Form 2916); Druckexemplar; Minutes of oral proceedings; Annex I-III.
EPO Appeal T1784/15-3.3.04, Opposition against EP 2 007 809, Opponent Glaxo Group Limited Notice of Appeal filed Sep. 10, 2015 (1 page).
EPO Appeal T1784/15-3.3.04, Opposition against EP 2 007 809, EPO Boards of Appeal Processing of Appeal signed Sep. 11, 2015 (2 pages).
EPO Appeal T1784/15-3.3.04, Opposition against EP 2 007 809, Opponent Novartis AG Notice of Appeal filed Sep. 14, 2015 (2 pages).
EPO Appeal T1784/15-3.3.04, Opposition against EP 2 007 809, EPO Boards of Appeal Communication dated Sep. 16, 2015 regarding Commencement of Proceedings before the Boards of Appeal in response to Notice of Appeal filed by Opponent Glaxo Group Limited (4 pages).
EPO Appeal T1784/15-3.3.04, Opposition against EP 2 007 809, EPO Boards of Appeal Communication dated Sep. 18, 2015 regarding Commencement of Proceedings before the Boards of Appeal in response to Notice of Appeal filed by Opponent Novartis AG (1 page).
EPO Appeal T1784/15-3.3.04, Opposition against EP 2 007 809, EPO Boards of Appeal Communication dated Nov. 13, 2015 regarding Composition of EPO Boards of Appeal (1 page).
EPO Appeal T1784/15-3.3.04, Opposition against EP 2 007 809, Patentee F. Hoffmann-La Roche Response to Observations on the Grounds of Appeal filed by Opponents Novartis AG and Glaxo Group Limited, filed Apr. 7, 2016 (163 pages) including: Main Request; Auxiliary Requests I to V; D46: Declarations of Dr. Dietmar Reusch and Markus Haberger (including Exhibits 1-3): Ex. 1—CV of Dr. Dietmar Reusch, Ex. 2—CV of Markus Haberger, Ex. 3—Summary Glyko all <IGF-1R>; D47: Declaration of Dr. Tilman Schlothauer (including Exhibits 1-7): Ex. 1—CV of Dr. Tilman Schlothauer, Ex. 2—Okazaki et al., "Fucose depletion from human IgG1 oligosaccharide enhances binding enthalpy and association rate between IgG1 and FcgammaRIIIa", J Mol Biol., 336(5):1239-1249 (2004), Ex. 3—Dall'Ozzo et al., "Rituximab-dependent cytotoxic-

(56) References Cited

OTHER PUBLICATIONS ity by natural killer cells: influence of FCGR3A polymorphism on the concentration-effect relationship", Cancer Res., 64(13):4664-4669 (2004), Ex. 4—Hogarth et al., "Fc receptor-targeted therapies for the treatment of inflammation, cancer and beyond", Nat Rev Drug Discov., 11(4):311-331 (2012), Ex. 5—Golay et al., "Glycoengineered CD20 antibody obinutuzumab activates neutrophils and mediates phagocytosis through CD16B more efficiently than rituximab", Blood, 122(20):3482-3491 (2013), Ex. 6—Dashivets et al., "Multi-Angle Effector Function Analysis of Human Monoclonal IgG Glycovariants", PLoS One, 10(12):e0143520 (2015), Ex. 7—Results of experiment.
EPO Appeal T1784/15-3.3.04, Opposition against EP 2 007 809, Patentee F. Hoffmann-La Roche Further Submission regarding Corrected Version of Updated List of Documents (Amex A) including Updated List of Documents (Annex A), filed Apr. 8, 2016 (5 pages).
EPO Appeal T1784/15-3.3.04, Opposition against EP 2 007 809, EPO Boards of Appeal Communication of the Registry dated Apr. 15, 2016 (2 pages).
EPO Appeal T1784/15-3.3.04, Opposition against EP 2 007 809, Opponent Novartis AG Request for Accelerated Processing before the Boards of Appeal filed Nov. 4, 2016 (23 pages) including: Package Leaflet: Information for the user—Ilaris 150 mg powder for solution for injection Canakinumab; Case Management Order II in the civil case, F. Hoffmann-La Roche Aktiengesellschaft versus Novartis Pharma Gesellschaft mit beschränkter Haftung and others, dated Oct. 12, 2016, Civil Chamber 4a, Presiding Judge at the Regional Court in German with English Translation.
EPO Appeal T1784/15-3.3.04, Opposition against EP 2 007 809, EPO Boards of Appeal Summons to Oral Proceedings pursuant to Article Rule 115(1) EPC and Communication of the Boards of Appeal regarding Reply to Opponent Novartis Request for Acceleration of Present Appeal Proceedings dated Nov. 21, 2016 (4 pages).
EPO Appeal T1784/15-3.3.04, Opposition against EP 2 007 809, Patentee F. Hoffmann-La Roche response to the Summons to Oral Proceedings, filed Dec. 2, 2016 (270 pages) including: New Auxiliary Requests 1 to 53; D51: DrugBank: Basiliximab (http://www.drugbank.ca/drugs/DB00074); D52: WO 2005/005635 A2 A3; D53: EMA product information on Simulect—Annex I—Summary of Product Characteristics, Annex II—Manufacturers of the Biological Active Substance and Manufacturing Authorization Holder Responsible for Batch Release; Conditions of the Marketing Authorisation, Annex III—Labelling and Package Leaflet; D54: Vezer et al., "Authorized manufacturing changes for therapeutic monoclonal antibodies (mAbs) in European Public Assessment Report (EPAR) documents", Curr Med Res Opin., 32(5):829-834 (2016); Annex I—Amendments in new Auxiliary Requests 1 to 53 Table.
EPO Appeal T1784/15-3.3.04, Opposition against EP 2 007 809, Opponent Glaxo Group Limited Response to EPO Boards of Appeal Oral Proceedings pursuant to Article Rule 115(1) EPC, filed Jan. 17, 2017 (1 page).
EPO Appeal T1784/15-3.3.04, Opposition against EP 2 007 809, Opponent Novartis AG Further Submissions From O1 filed Mar. 24, 2017 (31 pages) including: D55: Reusch et al., "Comparison of methods for the analysis of therapeutic immunoglobulin G Fc-glycosylation profiles—Part 2: Mass spectrometric methods," mAbs 7(4):732-742 (2015); D56: Reusch et al., "Fc glycans of therapeutic antibodies as critical quality attributes," Glycobiology 25(12):1325-1334 (2015).
EPO Appeal T1784/15-3.3.04, Opposition against EP 2 007 809, Opponent Novartis AG Further Submissions From O1 filed Apr. 21, 2017 (32 pages) including: D57: Sworn Statement of Sercan Tarharci; D58: Sworn Statement of Mauela Weidner; D59: Sworn Statement of Matthias Berg; D60: US 2002/0106370 A1.
EPO Appeal T1784/15-3.3.04, Opposition against EP 2 007 809, Patentee F. Hoffmann-La Roche Response to Submissions filed by Opponent Novartis AG (Opponent 1), filed May 9, 2017 (110 pages) including: New Ausiliary Requests 1 to 35; Annex I—Amendments in new Auxiliary Requests 1 to 35 Table; D61: Declaration of Dr. Dietmar Reusch; Consolidated list of cited documents.
EPO Appeal T1784/15-3.3.04, Opposition against EP 2 007 809, Opponent Novartis AG Further Submissions From O1 filed Jun. 5, 2017 (42 pages) including: D62: Sworn Statement of Sercan Tarhanci; D63: Wolfenden et al., "Rates of spontaneous cleavage of glucose, fructose, sucrose, and trehalose in water, and the catalytic proficiencies of invertase and trehalas", J Am Chem Soc., 130(24):7548-7549 (2008); D64: Lin et al., "A common glycan structure on immunoglobulin G for enhancement of effector functions", Proc Natl Acad Sci U.S.A., 112(34):10611-10616 (2015); D65: Ferrara et al., "Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II", Biotechnol Bioeng., 93(5):851-861 (2006); D66: Geisse et al., "Large-scale transient transfection of mammalian cells: a newly emerging attractive option for recombinant protein", J Struct Funct Genomics, 6(2-3):165-170 (2005); D67: Rominger et al., "Characterization of [$^{125}$I]sauvagine binding to CRH2 receptors: membrane homogenate and autoradiographic studies", J Pharmacol Exp Ther., 286(1):459-468 (1998).
EPO Appeal T1784/15-3.3.04, Opposition against EP 2 007 809, EPO Boards of Appeal Communication regarding Communication of the Boards of Appeal pursuant to Article 15(1) of the Rules of Procedure of the Board of Appeal—Provisional Opinion dated Jun. 8, 2017 (7 pages).
EPO Appeal T1784/15-3.3.04, Opposition against EP 2 007 809, Opponent Novartis AG Submission filed Jun. 20, 2017 (1 page).
EPO Appeal T1784/15-3.3.04, Opposition against EP 2 007 809, Opponent Novartis AG (Opponent O1) Submission regarding withdrawal of its appeal filed Jun. 21, 2017 by post only (1 page).
EPO Appeal T1784/15-3.3.04, Opposition against EP 2 007 809, Opponent Novartis AG Submission regarding withdrawal of its opposition filed Jun. 22, 2017 by fax only (1 page).
EPO Appeal T1784/15-3.3.04, Opposition against EP 2 007 809, EPO Boards of Appeal Communication dated Jun. 26, 2017 with copy of the minutes of the oral proceedings (3 pages).
Action for Infringement by F. Hoffmann-La Roche AG against Novartis Pharma Gmbh and Novartis AG dated Sep. 27, 2016 in German with English Translation (191 pages), including: Exhibit K1: EP 2007809 B1 (patent-in-suit); Exhibit K2: Ground for Decision of Opposition in EP Application 07724105.7 (EP2007809) dated Jul. 13, 2015, in English with German translation; Exhibit K3: EP 2007809 B1 (patent-in-suit), in English with German translation; Exhibit K4: Exhibit K4 in German with English translation of K4 as shown on pp. 12-13 of the English translation of the Action for Infringement by F. Hoffmann-La Roche AG dated Sep. 27, 2016; Exhibit K5: article of the Deutsche ApothekerZeitung, in German with English translation; Exhibit K6: Delivery Note dated Aug. 18, 2016, in German with English translation; Exhibit K7: Summary of Product Characteristics of Ilaris®, in German with UK equivalent of Summary of Product Characteristics of Ilaris®; Exhibit K8: Measurement of Canakinumab (LotS0079) corresponding to Table 3A EP 2007809 B1, in German with English translation; Exhibit K9: Extract of the Novartis Website, in German with English translation.
Novartis et al. Response to Complaint in the case F. Hoffmann-La Roche AG vs. Novartis Pharma Gmbh and Novartis AG, dated Feb. 15, 2017, in German with English translation (231 pages), including: Exhibit TW4: Ilaris—Glossary, in German with English translation; Exhibit TW5: Ilaris—Glycan, in German with English translation; Exhibit TW6: rel. amount of glycostructures, in German with English translation; Exhibit TW7: Declaration of Dr. Kurt Forrer (D48) in the Appeal T1784/15 of Opposition against EP 2007809; Exhibit TW8: EP 1313769 B2; Exhibit TW9: DE 60124863 T3, German translation of EP 1248804 B2; Exhibit TW10: Pharmazeutische Zeitung, Canakinumab, "Antibody against rare hereditary disease" by Kerstin A. Gräfe, in German with English translation.
F. Hoffmann-La Roche AG Reply in the case, *F. Hoffmann-La Roche AG* vs. *Novartis Pharma Gmbh and Novartis AG*, dated May 30, 2017, in German with English translation (200 pages), including: Exhibit K10: Center for Drug Evaluation and Research—

(56) References Cited

OTHER PUBLICATIONS

Pharmacology Review(s)—Supervisory Pharmacologist Memorandum (BLA No. 125319) for Ilaris® (Canakinumab); Exhibit K11: Pharmacology/Toxicology Review and Evaluation (BLA No. 125319) for Ilaris™ (Canakinumab); Exhibit K12: RAJU, "Glycosylation Variations with Expression Systems and Their Impact on Biological Activity of Therapeutics Immunoglobulins", BioProcess International :44-53 (Apr. 2003); Exhibit K13: The oligosaccharides considered in example 3 according to Table 3a and 3b of the patent-in-suit, in German with English translation; Exhibit K14: Sworn Statement by Matthias Berg; Exhibit K15: Original values by Novartis of Exhibit TW6 if evaluated according to Example 3 of the patent-in-suit, i.e. without taking into account Man 6, G0-F-N and G1-F-N, in German with English translation; Exhibit K16: Chakraborty et al., "Pharmacokinetic and pharmacodynamic properties of canakinumab, a human anti-interleukin-1β monoclonal antibody", Clin Pharmacokinet, 51(6):e1-18 (2012); Exhibit K17: Lachmann et al., "Use of canakinumab in the cryopyrin-asscociated periodic syndrome", N Engl J Med., 360(23):2416-2425 (2009); Exhibit K18: ClinicalTrials.gov—Study NCT00465985 "Efficacy, Safety, and Tolerability of ACZ885 in Patients With Muckle-Wells Syndrome (REMITTER)"; Exhibit K19: Vezer et al., "Authorized manufacturing changes for therapeutic monoclonal antibodies (mAbs) in European Public Assessment Report (EPAR) documents", Curr Med Res Opin., 32(5):829-834 (2016).
Decision by the Regional Court Dusseldorf in the matter of F. Hoffmann-La Roche AG versus Novartis Pharma GmbH and others, dated Jul. 10, 2017, in German with English translation (2 page).
Chilean Search Report for corresponding Application 1020-2007 (19 pages).
Chilean Search Report for corresponding Application 1020-2007 (10 pages).
Japanese Office Action in corresponding Application 2009-504627 (dated Jun. 27, 2011) (6 pages).
Office Action in U.S. Appl. No. 11/784,029 (dated Aug. 6, 2008) (20 pages).
Office Action in U.S. Appl. No. 11/784,029 (dated Mar. 18, 2009) (15 pages).
Bihoreau et al., "Combination of Capillary Electrophoresis and Matrix-assisted Laser Desorption Ionization Mass Spectrometry for Glycosylation Analysis of a Human Monoclonal Anti-Rhesus(D) Antibody," Journal of Chromatography B, 697:123-133 (1997).
Ferrara et al., "The Carbohydrate at FcγRIIIa Asn-162 an Element Required for High Affinity Binding to Non-Fucosylated IgG Glycoforms," The Journal of Biological Chemistry, 281(8):5032-5036 (2006).
*Takeda UK Limited* vs. *F. Hoffmann-La Roche AG*, Particulars of Claim filed in the High Court of Justice Business and Property Courts of England and Wales, Claim No. HP-2018-000008, dated Apr. 11, 2018 (3 pages).
*Takeda UK Limited* vs. *F. Hoffmann-La Roche AG*, Grounds of Invalidity filed in the High Court of Justice Business and Property Courts of England and Wales, Claim No. HP-2018-000008, dated Apr. 11, 2018 (7 pages).
EPO Appeal T1784/15-3.3.04, Decision dated Jun. 22, 2017 (47 pages).
*Takeda GmbH* v. *F. Hoffman-La Roche AG*, Nullity Complaint, dated Jun. 8, 2018 (101 pages) (with English translation, 98 pages) including exhibits: NIK1—EP 2 007 809 B1; NIK1b—WO 2007/115813 (Original PCT patent application from which the patent in suit emerged); NIK2—Printout from the DPMA Register on the German portion of NIK1 (DE 60 2007 025 417.5); NIK3—Transcript of the oral hearing before the EPO Board of Appeal on the opposition proceeding concerning EP 2 007 809 B1; NIK4—Version of the claims of EP 2 007 809 B1 upheld in the opposition proceeding before the EPO to a limited extent; NIK5—Bihoreau et al., J Chromatogr B Biomed Sci Appl. Sep 12, 1997;697(1-2):123-33; NIK6—Ferrara et al., J Biol Chem. Feb. 24, 2006;281(8):5032-6. Epub Dec. 5, 2005; NIK7—Durocher et al., Nucleic Acids Res. Jan. 15, 2002;30(2):E9; NIK8—Beck et al., J Chromatogr B Analyt Technol Biomed Life Sci. May 25, 2005;819(2):203-18; NIK9—Huang et al., Anal Biochem. Feb. 15, 2006;349(2):197-207. Epub Nov. 28, 2005; NIK10a—Statement of Dr. Kurt Forrer; NIK10b—Statement of Matthias Berg; NIK10c—Statement of Nicolas Naula; NIK10d—Document describing deliveries of the SIMULECTTM antibody in Italy; NIK10e—Statement of Sercan Tarhanci; NIK10f—Statement of Manuela Weidner; NIK10g—Statement of Sercan Tarhanci; NIK11—WO 2005/040221 A1; NIK11b—English translation of NIK11; NIK11c—Translation certificate for NIK11b; NIK12—EP 1 176 195 A1; NIK13—Raju, BioProcess International, Apr. 2003, pp. 44-53; NIK14—Shinkawa et al., The Journal of Biological Chemistry, vol. 278, No. 5, Issue of Jan. 31, pp. 3466-3473, 2003; NIK15a—Wagner-Rousset et al., J Chromatogr B Analyt Technol Biomed Life Sci. Sep. 1, 2008; 872(1-2):23-37; NIK16—Kingston RE et al, Curr Protoc Mol Biol., 2002, Chapter 16, Unit 16.23; NIK17—Statement of Silke Hansen; NIK18—Textbook excerpt: Salvatore Fanali, et al., "Liquid Chromatography: Applications," Handbooks in Separation Science, Elsevier, USA, 2013; pp. 188-189; NIK19—WO 98/06248; NIK20—Ihara et al., Glycobiology. Apr. 2006;16(4):333-42. Epub Dec. 11, 2005; NIK21—EP 1 333 032 A1; NIK22—US 2003/0115614; NIK23—Matsumiya et al., J Mol Biol. May 4, 2007; 368(3):767-79. Epub Feb. 22, 2007; NIK24—Reusch et al., MAbs. Jul.-Aug. 2015; 7(4): 732-742; NIK24a—Hu et al., J Mass Spectrom. Apr. 2005;40(4):430-43; NIK25—EP 2007810 B1; NIK26—Statement by Dietmar Reusch; NIK27—Statement by M. Patel; NIK28—Sinha et al., J Am Soc Mass Spectrom. Nov. 2008;19(11):1643-54; NIK29—Expert opinion by Prof. Dr. Friedrich Altmann; NIK29a—Declaration by Caterina Farnleitner; NIK30—Notification by the Registrar's Office of the EPO's Boards of Appeal of May 3, 2018; NIK31—Judicial procedural control order by Patent Litigation Chamber 4b of the Regional Court Dusseldorf; NIK32—Order by the Chamber of the Regional Court Dusseldorf of Apr. 16, 2018; NIK33—Excerpt from the infringement complaint by F. Hoffmann-La Roche AG against Nullity Plaintiff; NIK34—Gennaro and Salas-Solano, Anal. Chem. 2008, 80, 3838-3845.
*Takeda Pharmaceuticals U.S.A., Inc., Takeda Pharmaceuticals America, Inc.*, and *Millennium Pharmaceuticals, Inc.*, v. *Genetech, Inc.*, C.A. No. 2018-0384-JTL, In the Court of Chancery of the State of Delaware Plaintiffs' Brief in Opposition to Genentech, Inc.'s Motion to Dismiss, dated Aug. 22, 2018.
Exhibit B1—*Takeda Pharmaceuticals U.S.A., Inc., Takeda Pharmaceuticals America, Inc.*, and *Millennium Pharmaceuticals, Inc.*, v. *Genentech, Inc.*, C.A. No. 2018-0384-JTL, In the Court of Chancery of the State of Delaware, Plaintiffs' Complaint for Injunctive Relief, dated May 30, 2018.
Exhibit B3—Gomollón et al., "3rd European Evidence-based Consensus on the Diagnosis and Management of Crohn's Disease 2016: Part 1: Diagnosis and Medical Management," Journal of Crohn's and Colitis, 3-25 (2017).
Exhibit B4—Statement of the German Association for *Gastroenterology, Digestive and Metabolic Disease* [Deutsche Gellschaft für Gastroenterologie, Verdauungs—und Stoffwechselkrankheiten (DGVS](2015).
Exhibit B4(a)—English translation of Exhibit B4 (certification included).
Exhibit B5—Colombel et al., "The safety of vedolizumab for ulcerative colitis and Crohn's disease," Gut 0:1-13 (2016).
Exhibit B6—Exhibit A (42 pages).
Exhibit B6—Exhibit B (9 pages).
Exhibit B6—Exhibit C (9 pages).
Exhibit B6—Exhibit D (18 pages).
Exhibit B6—Exhibit E (6 pages).
Exhibit B6—Exhibit F (5 pages).
Exhibit B6—Exhibit G (10 pages).
Exhibit B6—Exhibit H (7 pages).
Exhibit B6—Exhibit I (147 pages).
Exhibit B6—Exhibit K (193 pages).
Exhibit B6—Exhibit L (275 pages).
Exhibit B6—Exhibit M (119 pages).
Exhibit B6—Exhibit N (22 pages).
Exhibit B6—Exhibit Q (163 pages).
Exhibit B6—Exhibit R (76 pages).

(56) References Cited

OTHER PUBLICATIONS

Exhibit B6—Exhibit S (167 pages).
Exhibit B7—Wyant et al., "In vitro assessment of the effects of vedolizumab binding on peripheral blood lymphocytes," mAbs 5(6):842-850, Nov./Dec. 2013.
Exhibit B8—Excerpt of Assessment Report EMA, dated Mar. 20, 2014.
Exhibit B9—Excerpt of the statement of defense in *F. Hoffmann-La Roche AG v. Novartis Pharma GmbH et al.*, Düsselfdorf District Court, 4a O 99/16.
Exhibit B9(a)—English translation of Exhibit B9 (certification included).
Exhibit B13—Excerpt of the online dictionary "*Merriam-Webster*" for the word "control".
Exhibit B14—Excerpt of *Genentech* website.
Roche Reply to Post Trial Submission, English Translation in German Court of First Instance of Düsselfdorf (Landgericht Düsselfdorf), Case No. 4b 07/18, dated Aug. 5, 2019 (22 pages).
Takeda Further_Submission, English Translation in German Court of First Instance of Düsselfdorf (Landgericht Düsselfdorf), Case No. 4b 07/18 dated Jul. 12, 2019 (29 pages).
Roche Action in German Court of First Instance of Düsselfdorf (Landgericht Düsseldorf), Case No. 4b 07/18 dated Feb. 2, 2018 (17 pages).
Takeda Statement of Defense, English Translation in German Court of First Instance of Düsselfdorf (Landgericht Düsseldorf), Case No. 4b 07/18 dated Jun. 11, 2018 (141 pages).
Roche Reply, English Translation in German Court of First Instance of Düsseldorf (Landgericht Düsseldorf), Case No. 4b 07/18 dated Dec. 20, 2018 (102 pages).
Takeda Antwort Reply, English Translation in German Court of First Instance of Düsseldorf (Landgericht Düsseldorf), Case No. 4b 07/18 dated Jun. 6, 2019 (143 pages).
Roche Surrejoinder, English Translation in German Court of First Instance of Düsseldorf (Landgericht Düsseldorf), Case No. 4b 07/18 dated Jul. 8, 2019 (39 pages).
Judgement, English Translation in German Court of First Instance of Düsseldorf (Landgericht Düsseldorf), Case No. 4b 07/18 dated Sep. 20, 2019 (54 pages).
Appeal and Substantiation of Appeal, English Translation in German Court of First Instance of Düsselfdorf (Landgericht Düsseldorf), Case No. 4b 07/18 dated Oct. 21, 2019 (45 pages).
Exhibit B40 in German Court of First Instance of Düsseldorf (Landgericht Düsseldorf), Case No. 4b 07/18 dated Oct. 21, 2019 (7 pages).
Exhibit B41 in German Court of First Instance of Düsseldorf (Landgericht Düsseldorf), Case No. 4b 07/18 dated Oct. 21, 2019 (7 pages).
Exhibit B42 in German Court of First Instance of Düseldorf (Laandgericht Düsseldorf), Case No. 4b 07/18 dated Oct. 21, 2019 (8 pages).
Exhibit B43 in German Court of First Instance of Düseldorf (Landgericht Düsseldorf), Case No. 4b 07/18 dated Oct. 21, 2019 (5 pages).
Takeda Post Trial submission in German Court of First Instance of Düsseldorf (Landgericht Düsseldorf), Case No. 4b 07/18 dated Jul. 30, 2019 (23 pages).
Takeda Klageschrift Nullity Suit, English Translation in German Federal Patent Court (Bundespatentgericht), Case No. 3, Ni 12/18 (EP) dated Jun. 8, 2018 (98 pages).
Takeda TBK Entscheidung, English Translation in German Federal Patent Court (Bundespatentgericht), Case No. 3 Ni 12/18 (EP) dated Jul. 24, 2018 ( 8 pages)
Roche English Translation of Nachreichung Dokumente Submission of further Docs in German Federal Patent Court (Bundespatentgericht), Case No. 3 Ni 12/18 (EP) dated Dec. 20, 2018 (1 page).
Roche English Translaation of Widerspruchsbegründung Reply in German Federal Patent Court (Bundespatentgericht), Case No. 3 Ni 12/18 (EP) dated Dec. 20, 2018 (71 pages).
Takeda English Translation of Antwort Reply in German Federal Patent Court (Bundespatentgericht), Case No. 3 Ni 12/18 (EP) dated Jun. 6, 2019 (90 pages).
Takeda English Translation of Submission Schriftsatz in German Federal Patent Court (Bundespatentgericht), Case No. 3 Ni 12/18 (EP) dated Dec. 2, 2019 (17 pages).
NIK57 in German Federal Patent Court (Bundespatentgericht), Case No. 3 Ni 12/18 (EP) dated Dec. 2, 2019 (48 pages).
NIK58 in German Federal Patent Court (Bundespatentgericht), Case No. 3 Ni 12/18 (EP) dated Dec. 2, 2019 (7 pages).
NIK59 in German Federal Patent Court (Bundespatentgericht), Case No. 3 Ni 12/18 (EP) dated Dec. 2, 2019 (5 pages).
NIK60 in German Federal Patent Court (Bundespatentgericht), Case No. 3 Ni 12/1 (EP) dated Dec. 2, 2019 (1 page).
Complaint against Takeda English Translation in Commercial Court No. 4 of Barcelona (Spain), Case No. 1868/2019 dated Sep. 25, 2019 (59 pages).
Decision in Commercial Court No. 4 of Barcelona (Spain), Case No. 1868/2019 dated Sep. 30, 2019 (7 pages).
Takeda Reply and Counterclaim, English Translation in Commercial Court No. 4 of Barcelona (Spain), Case No. 1868/2019 dated Dec. 12, 2019 (133 pages).
Hoffmann Laroche Takeda Delpharm 1Memorial183, English Translation in Turin Court (Italy)—Chamber Sepcialized in Enterprise, Case No. 18375/2018 dated Feb. 1, 2019 (12 pages).
Hoffmann Laroche Takeda Delpharm 1Memoriatecnica, English Translation in Turin Court (Italy)—Chamber Specialized in Enterprise, Case No. 18375/2018 dated Sep. 30, 2019 (43 pages).
Hoffmann Laroche Takeda Delpharm 2Memoria183, English Translation in Turin Court (Italy)—Chamber Specialized in Enterprise, Case No. 19375/2018 dated Mar. 4, 2019 (15 pages).
Hoffmann Laroche Takeda Delpharm 2Memoritatecnica, English Translation in Turin Court (Italy)—Chamber Specialized in Enterprise, Case No. 18375/2018 dated Nov. 15, 2019 (48 pages).
Hoffmann Laroche Takeda Delpharm 3Memoria183, English Translation in Turin Court (Italy)—Chamber Specialized in Enterprise, Case No. 18375/2018 dated Mar. 21, 2019 (12 pages).
Hoffmann Laroche Takeda Delpharm 3Memoriatecnica, English Translation in Turin Court (Italy)—Chamber Specialized in Enterprise, Case No. 18375/2018 dated Dec. 9, 2019 (23 pages).
Hoffmann Laroche Takeda Delpharm Citazione, English Translation in Turin Court (Italy)—Chamber Specialized in Enterprise, Case No. 18375/2018 dated Jul. 27, 2018 (18 paages).
Takeda Delpharm Hoffmann Laroche 1Memoria183, English Translation in Turin Court (Italy)—Chamber Specialized in Enterprise, Case No. 18375/2018 dated Jan. 31, 2019 (11 pages).
Takeda Delpharm Hoffmann Laroche 1Memoriatecnica, English Translation in Turin Court (Italy)—Chamber Specialized in Enterprise, Case No. 18375/2018 dated Sep. 30, 2019 (161 pages).
Takeda Delpharm Hoffmann Laroche 2Memorial183, English Translation in Turin Court (Italy)—Chamber Specialized in Enterprise, Case No. 18375/2018 dated Mar. 4, 2019 (15 pages).
Takeda Delpharm Hoffmann Laroche 2Memoriatecnica, English Translation in Turin Court (Italy)—Chamber Specialized in Enterprise, Case No. 18375/2018 dated Nov. 15, 2019 (50 pages).
Takeda Delpharm Hoffmann Laroche 3Memorial183, English Translation in Turin Court (Italy)—Chamber Specialized in Enterprise, Case No. 18375/2018 dated Mar. 25, 2019 (21 pages).
Takeda Delpharm Hoffmann Laroche 3Memoriatecnica, English Translation in Turin Court (Italy)—Chamber Specialized in Enterprise, Case No. 18375/2018 dated Dec. 9, 2019 (35 pages).
Takeda Delpharm Hoffmann Laroche Costituzione, English Translation in Turin Court (Italy)—Chamber Specialized in Enterprise, Case No. 18375/2018 dated Nov. 22, 2018 (43 pages).
Takeda Delpharm Hoffmann Laroche Istanza, English Translation in Turin Court (Italy)—Chamber Specialized in Enterprise, Case No. 18375/2018 dated Nov. 22, 2018 (3 pages).
Exhibit CF1 DSMZ delivery note in U.K. High Court of Justice, Case No. HP-2018-000008 dated Feb. 11, 2019 (4 pages).
Exhibit AK 1 in U.K. High Court of Justice, Case No. HP-2018-000008 dated Feb. 15, 2019 (12 pages).
Exhibit AK 2 in U.K. High Court of Justice, Case No. HP-2018-000008 dated Feb. 15, 2019 (17 pages).

(56) References Cited

OTHER PUBLICATIONS

Exhibit AK 3 in U.K. High Court of Justice, Case No. HP-2018-000008 dated Feb. 15, 2019 (6 pages).
Exhibit AK 4 in U.K. High Court of Justice, Case No. HP-2018-000008 dated Feb. 15, 2019 (7 pages).
Exhibit AK 5 WO9806248 U.K. in High Court Justice, Case No. HP-2018-000008 dated Feb. 15, 2019 (148 pages).
Exhibit AK 6 in U.K. High Court of Justice, Case No. HP-2018-000008 dated Apr. 10, 2019 (4 pages).
Exhibit AK 7 in U.K. High Court of Justice, Case No. HP-2018-000008 dated Apr. 10, 2019 (30 pages).
Exhibit AK 8 WO2007061679 in U.K. High Court of Justice, Case No. HP-2018-000008 dated Apr. 10, 2019 (77 pages).
Exhibit AK 10 in U.K. High Court of Justice, Case No. HP-2018-000008 dated Apr. 10, 2019 (36 pages).
Exhibit AK 11 in U.K. High Court of Justice, Case No. HP-2018-000008 dated Apr. 10, 2019 (4 pages).
Exhibit B2 1 in U.K. High Court of Justice, Case No. HP-2018-000008 dated May 21, 2019 (34 pages).
Exhibit CB 1 CV in U.K. High Court of Justice, Case No. HP-2018-000008 dated Apr. 14, 2019 (32 pages).
Exhibit CB 2 CGK in U.K. High Court of Justice, Case No. HP-2018-000008 dated Apr. 14, 2019 (31 pages).
Exhibit CB 3 INN for Basiliximab in U.K. High Court of Justice, Case No. HP-2018-000008 dated Apr. 14, 2019 (2 pages).
Exhibit CB 4 SmPC for Basiliximab Simulect in U.K. High Court of Justice, Case No. HP-2018-000008 dated Apr. 14, 2019 (45 pages).
Exhibit CB 5 FDA approved therapeutic monoclonal antibodies in U.K. High Court of Justice, Case No. HP-2018-000008 dated May 16, 2019 (2 pages).
Exhibit CB 6 Li PNAS 2017 in U.K. High Court of Justice, Case No. HP-2018-000008 dated May 16, 2019 (9 pages).
Exhibit CB 7 The Journal of Biological Chemistry Editorial Policies in U.K. High Court of Justice, Case No. HP-2018-000008 dated May 16, 2019 (22 pages).
Exhibit CF 2 InVivo receipt of cells in U.K. High Court of Justice, Case No. HP-2018-000008 dated Feb. 11, 2019 (2 pages).
Exhibit CF 3 InVivo certificate of analysis in U.K. High Court of Justice, Case No. HP-2018-000008 dated Feb. 11, 2019 (3 pages).
Exhibit FN 1 CV in U.K. High Court of Justice, Case No. HP-2018-000008 dated Apr. 15, 2019 (13 pages).
Exhibit FN 2 Kinetic Approach Plots in U.K. High Court of Justice, Case No. HP-2018-000008 dated Apr. 24, 2019 (25 pages).
Exhibit FN 3 Equilibrium Approach Plots in U.K. High Court of Justice, Case No. HP-2018-000008 dated Apr. 24, 2019 (7 pages).
Exhibit FN 4 Lux et al 2013 in U.K. High Court of Justice, Case No. HP-2018-000008 dated Jun. 3, 2019 (10 pages).
Exhibit FN 5 Kao et al 2015 in U.K. High Court of Justice, Case No. HP-2018-000008 dated Jun. 3, 2019 (12 pages).
Exhibit HRM 1 CV in U.K. High Court of Justice, Case No. HP-2018-000008 dated Arp. 12, 2019 (55 pages).
Exhibit HRM 2 in U.K. High Court of Justice, Case No. HP-2018-000008 dated Apr. 12, 2019 (3 pages).
Exhibit HR, 3 in U.K. High Court of Justice, Case No. HP-2018-000008 dated Apr. 12, 2019 (2 pages).
Exhibit HRM 4 in U.K. High Court of Justice, Case No. HP-2018-000008 dated Apr. 12, 2019 (2 pages).
Exhibit HRM 5 in U.K. High Court of Justice, Case No. HP-2018-000008 dated Apr. 12, 2019 (2 pages).
Exhibit HRM 6 in U.K. High Court of Justice, Case No. HP-2018-000008 dated Apr. 12, 2019 (15 pages).
Exhibit HRM 7 in U.K. High Court of Justice, Case No. HP-2018-000008 dated May 17, 2019 (9 pages).
Exhibit HRM 8 in U.K. High Court of Justice, Case No. HP-2018-000008 dated May 17, 2019 (9 pages).
Exhibit HRM 11 in U.K. High Court of Justice, Case No. HP-2018-000008 dated Jun. 7, 2019 (3 pages).
Exhibit HRM 12 in U.K. High Court of Justice, Case No. HP-2018-000008 dated Jun. 7, 2019 (21 pages).
Exhibit HRM 13 in U.K. High Court of Justice, Case No. HP-2018-000008 dated Jun. 7, 2019 (2 pages).
Exhibit MB 1 CV in U.K. High Court of Justice, Case No. HP-2018-000008 dated Apr. 12, 2019 (36 pages).
Exhibit MB 2 Raju Glycobiology 2000 in U.K. High Court of Justice, Case No. HP-2018-000008 dated Apr. 12, 2019 (11 pages).
Exhibit MB 3 Butler Cytotechnology 2006 in U.K. High Court of Justice, Case No. HP-2018-000008 dated Apr. 12, 2019 (21 pages).
Exhibit MB 4 Raju BioProcess International 2003 in U.K. High Court of Justice, Case No. HP-2018-000008 dated Apr. 12, 2019 (9 pages).
Exhibit MB 5 Shields Journal of Biolgocial Chemistry 2002 in U.K. High Court of Justice, Case No. HP-2018-000008 dated Apr. 12, 2019 (10 pages).
Exhibit MB 6 Beck Chromatography B 2005 in U.K. High Court of Justice, Case No. HP-2018-000008 dated Apr. 12, 2019 (17 pages).
Exhibit MB 7 Fugene protocol 2006 in U.K. High Court of Justice, Case No. HP-2018-000008 dated Apr. 12, 2019 (7 pages).
Exhibit MB 8 Jacobsen Methods 2004 in U.K. High Court of Justice, Case No. HP-2018-000008 dated Apr. 12, 2019 (10 pages).
Exhibit MB 9 ECACC profile for CHO K1 cells in U.K. High Court of Justice, Case No. HP-2018-000008 dated May 17, 2019 (3 pages).
Exhibit MB 10 Xu Nat Biotechnol 2012 in U.K. High Court of Justice, Case No. HP-2018-000008 dated May 17, 2019 (22 pages).
Exhibit MB 11 WO00066604 in U.K. High Court of Justice, Case No. HP-2018-000008 dated May 17, 2019 (15 pages).
Exhibit MB 12 EP0449769B1 in U.K. High Court of Justice, Case No. HP-2018-000008 dated May 17, 2019 (39 pages).
Exhibit MB 13 SmPC for Basiliximab in U.K. High Court of Justice, Case No. HP-2018-000008 dated May 17, 2019 (45 pages).
Exhibit MC 1 CV in U.K. High Court of Justice, Cae No. HP-2018-000008 dated Apr. 15, 2019 (21 pages).
Exhibit MC 2 Roche Method Table 3b compared to Takeda Notice of Experiments in U.K. High Court of Justice, Case No. HP-2018-000008 dated Apr. 15, 2019 (2 pages).
Exhibit PP 1 CV in U.K. High Court of Justice, Case No. HP-2018-000008 dated Apr. 12, 2019 (38 pages).
Exhibit PP 2 in U.K. High Court of Justice, Case No. HP-2018-000008 dated Apr. 12, 2019 (9 pages).
Exhibit PP 3 in U.K. High Court of Justice, Case No. HP-2018-000008 dated May 17, 2019 (4 pages).
Exhibit PP 4 in U.K. High Court of Justice, Case No. HP-2018-000008 dated May 17, 2019 (2 pages).
Exhibit PP 5 in U.K. High Court of Justice, Case No. HP-2018-000008 dated May 17, 2019 (58 pages).
Exhibit PP 6 in U.K. High Court of Justice, Case No. HP-2018-000008 dated May 17, 2019 (49 pages).
Exhibit PP 7 in U.K. High Court of Justice, Case No. HP-2018-000008 dated May 17, 2019 (61 pages).
Exhibit PP 8 in U.K. High Court of Justice, Case No. HP-2018-000008 dated Jun. 7, 2019 (8 pages).
Exhibit PP 9 in U.K. High Court of Justice, Case No. HP-2018-000008 dated Jun. 7, 2019 (79 pages).
Exhibit PP 10 in U.K. High Court of Justice, Case No. HP-2018-000008 dated Jun. 7, 2019 (10 pages).
Exhibit PP 11 in U.K. High Court of Justice, Case No. HP-2018-000008 dated Jun. 7, 2019 (3 pages).
Exhibit PP 12 in U.K. High Court of Justice, Case No. HP-2018-000008 dated Jun. 7, 2019 (36 pages).
Exhibit PP 13 in U.K. High Court of Justice, Case No. HP-2018-0000008 dated Jun. 7, 2019 (13 pages).
Exhibit PP 14 in U.K. High Court of Justice, Case No. HP-2018-000008 dated Jun. 7, 2019 (15 pages).
Exhibit PP 15 in U.K. High Court of Justice, Case No. HP-2018-000008 dated Jun. 7, 2019 (10 pages).
Exhibit PP 16 in U.K. High Court of Justice, Case No. HP-2018-000008 dated Jun. 7, 2019 (12 pages).
Exhibit PP 17 in U.K. High Court of Justice, Case No. HP-2018-000008 dated Jun. 19, 2019 (9 pages).
Expert Report of Carolyn Bertozzi in U.K. High Court of Justice, Case No. HP-2018-000008 dated Apr. 14, 2019 (58 pages).

(56) References Cited

OTHER PUBLICATIONS

Expert Report of Falk Nimmerjahn in U.K. High Court of Justice, Case No. HP-2018-000008 dated Apr. 15, 2019 (17 pages).
Expert Report of Howard Morris Inc. Annex 1 in U.K. High Court of Justice, Case No. HP-2018-000008 dated Apr. 12, 2019 (83 pages).
Expert Report of Max Crispin in U.K. High Court of Justice, Case No. HP-2018-000008 dated Apr. 15, 2019 (21 pages).
Expert Report of Michael Butler in U.K. High Court of Justice, Case No. HP-2018-000008 dated Apr. 12, 2019 (26 pages).
Expert Report of Paul Parren Incl Annex 1 2B in U.K. High Court of Justice, Case No. HP-2018-000008 dated Apr. 12, 2019 (73 pages).
Fourth Expert Report of Paul Parren in U.K. High Court of Justice, Case No. HP-2018-000008 dated Jun. 19, 2019 (5 pages).
Judgment in U.K. High Court of Justice, Case No. HP-2018-000008 dated Jul. 17, 2019 (97 pages).
Jun et al. 2005 in U.K. High Court of Justice, Case No. HP-2018-000008 (8 pages).
Prof Morris Response to the Claimant Written Questions Submitted under CPR Part 35 6 in U.K. High Court of Justice, Case No. HP-2018-000008 dated May 30, 2019 (3 pages).
Re Amended Defence and Counterclaim in U.K. High Court of Justice, Case No. HP-2018-000008 dated May 23, 2019 (5 pages).
Re Re Re Amended Grounds of Invalidity in U.K. High Court of Justice, Case No. HP-2018-000008 dated Jun. 24, 2019 (9 pages).
Reusch et al. 2015 in U.K. High Court of Justice, Case No. HP-2018-000008 (11 pages).
Roche Closing Submissions in U.K. High Court of Justice, Case No. HP-2018-000008 dated Jun. 24, 2019 (107 pages).
Roche Opening Skelton in U.K. High Court of Justice, Case No. HP-2018-000008 dated Jun. 7, 2019 (107 pages).
Second Expert Report of Carolyn Bertozzi in U.K. High Court of Justice, Case No. HP-2018-000008 dated May 16, 2019 (34 pages).
Second Expert Report of Falk Nimmerjahn in U.K. High Court of Justice, Case No. HP-2018-000008 dated May 16, 2019 (8 pages).
Second Expert Report of Howard Morrisin in U.K. High Court of Justice, Case No. HP-2018-000008 dated May 17, 2019 (21 pages).
Second Expert Report of Max Crispin in U.K. High Court of Justice, Case No. HP-2018-000008 dated Jun. 3, 2019 (8 pages).
Second Expert Report of Michael Butler in U.K. High Court of Justice, Case No. HP-2018-000008 dated May 17, 2019 (14 pages).
Second Expert Report of Paul Parren in U.K. High Court of Justice, Case No. HP-2018-000008 dated May 17, 2019 (44 pages).
Second Witness Statement of Ann Kowal in U.K. High Court of Justice, Case No. HP-2018-000008 dated Apr. 10, 2019 (14 pages).
Second Witness Statement of Pamela Brauer in U.K. High Court of Justice, Case No. HP-2018-000008 dated Jun. 5, 2019 (4 pages).
Supplementary Expert Report of Falk Nimmerjahn in U.K. High Court of Justice, Case No. HP-2018-000008 dated Apr. 24, 2019 (16 pages).
Takeda Closing Submissions in U.K. High Court of Justice, Case No. HP-2018-000008 dated Jun. 24, 2019 (158 pages).
Takeda Opening Skeleton in U.K. High Court of Justice, Case No. HP-2018-000008 dated Jun. 7, 2019 (132 pages).
Third Expert Report of Carolyn Bertozzi in U.K. High Court of Justice, Case No. HP-2018-000008 dated Jun. 3, 2019 (3 pages).
Third Expert Report of Falk Nimmerjahnin in U.K. High Court of Justice, Case No. HP-2018-000008 dated Jun. 3, 2019 (11 pages).
Third Expert Report of Howard Morris in U.K. High Court of Justice, Case No. HP-2018-000008 dated Jun. 7, 2019 (5 pages).
Third Expert Report of Paul Parren in U.K. High Court of Justice, Case No. HP-2018-000008 dated Jun. 7, 2019 (17 pages).
Witness Statement of Anne Kowal in U.K. High Court of Justice, Case No. HP-2018-000008 dated Feb. 15, 2019 (8 pages).
Witness Statement of Caterina Farnleitner in U.K. High Court of Justice, Case No. HP-2018-000008 dated Feb. 11, 2019 (3 pages).
Witness Statement of Dr. Bastian Zimmermann in U.K. High Court of Justice, Case No. HP-2018-000008 dated May 21, 2019 (3 pages).
Witness Statement of Friedrich Altmann in U.K. High Court of Justice, Case No. HP-2018-000008 dated Feb. 11, 2019 (2 pages).
Witness Statement of Pamela Brauer in U.K. High Court of Justice, Case No. HP-2018-000008 dated Feb. 15, 2019 (3 pages).
Exhibit B42 in German Court of First Instance of Düsseldorf (Landgericht Düssldorf), Case No. 4b 07/18 dated Oct. 21, 2019 (8 pages).
Exhibit B43 in German Court of First Instance of Düsseldorf (Landgericht Düsseldorf), Case No. 4b 07/18 dated Oct. 21, 2019 (5 pages).
Take Klageschrift Nullity Suit, English Translation in German Federal Patent Court (Bundespatentgericht), Case No. 3 Ni 12/18 (EP) dated Jun. 8, 2018 (98 pages).
Roche English Translation of Widerspruchsbegründung Reply in German Federal Patent Court (Bundespatentgericht), Case No. 3 Ni 12/18 (EP) dated Dec. 20, 2018 (71 pages).
NIK60 in German Federal Patent Court (Bundespatentgericht), Case No. 3 Ni 12/18 (EP) dated Dec. 2, 2019 (1 page).
Hoffmann Laroche Takeda Delpharm 1Memoria183, English Translation in Turin Court (Italy)—Chamber Specialized in Enterprise, Case No. 18375/2018 dated Feb. 1, 2019 (12 pages).
Hoffmann Laroche Takeda Delphaarm 1Memoriatecnica, English Translation in Turin Court (Italy)—Chamber Specialized in Enterprise, Case No. 18375/2018 dated Sep. 30, 2019 (43 pages).
Hoffmann Laroche Takeda Delpharm 2Memoria183, English Translation in Turin Court (Italy)—Chamber Specialized in Enterprise, Case No. 18375/2018 dated Mar. 4, 2019 (15 pages).
Hoffmann Laroche Takeda Delpharm 2Memoriatecnica, English Translation in Turin Court (Italy)—Chamber Specialized in Enterprise, Case No. 18375/2018 dated Nov. 15, 2019 (48 pages).
Hoffmann Laroche Takeda Delpharm Citazione, English Translation in Turin Court (Italy)—Chamber Specialized in Enterprise, Case No. 18375/2018 dated Jul. 27, 2018 (18 pages).
Takeda Delpharm Hoffmann Laroche 1Memoriatecnica, English Translaation in Turin Court (Italy)—Chamber Specialized in Enterprise, Case No. 18375/2018 dated Sep. 30, 2019 (161 pages).
Takeda Delpharm Hoffmann Laroche 2Memoria183, English Translation in Turin Court (Italy)—Chamber Specialized in Enterprise, Case No. 18375/2018 dated Mar. 4, 2019 (15 pages).
Takeda Delpharm Hoffmann Laroche 3Memoria183, English Translation in Turin Court (Italy)—Chamber Specialized in Enterprise, Case No. 18375/2018 dated Mar. 25, 2019 (21 pages).
Exhibit AK 5 WO9806248 U.K. in High Court of Justice, Case No. HP-2018-000008 dated Feb. 15, 2019 (148 pages).
Exhibit AL 8 WO200761679 in U.K. High Court of Justice, Case No. HP-2018-000008 dated Apr. 10, 2019 (77 pages).
Exhibit B2 1 in U.KL High Court of Justice, Case No. HP-2018-000008 dated May 21, 2019 (34 pages).
Exhibit CB 4 SmPC for Basiliximab Simulect in U.KL High Court of Justice, Case No. HP-2018-000008 dated Apr. 14, 2019 (45 pages).
Exhibit CB FDA approved therapeutic monoclonal antibodies in U.K. High Court of Justice, Case No. HP-2018-000008 dated May 16, 2019 (2 pages).
Exhibit HRM 1 CV in U.K. High Court of Justice, Case No. HP-2018-000008 dated Apr. 12, 2019 (55 pages).
Exhibit HRM 3 in U.K. High Court of Justice, Case No. HP-2018-000008 dated Apr. 12, 2019 (2 pages).
Exhibit MB 5 Shields Journal of Biological Chemistry 2002 in U.K. High Court of Justice, Case No. HP-2018-000008 dated Apr. 12, 2019 (10 pages).
Exhibit MB 6 Beck Chromatography B 2005 in U.K.P High Court of Justice, Case No. HP-2018-000008 dated Apr. 12, 2019 (17 pages).
Exhibit MC 1 CV in U.K. High Court of Justice, Case No. HP-2018-000008 dated Apr. 15, 2019 (21 pages).
Exhibit PP 1 CV U.K. High Court of Justice, Case No. HP-2018-000008 dated Apr. 12, 2019 (38 pages).
Exhibit PP 3 in U.K. High Court of Justice, Case No. HP-2018-000008 daated May 15, 2019 (4 pages).
Exhibit PP 13 in U.K. High Court of Justice, Case No. HP-2018-000008 dated Jun. 7, 2019 (13 pages).

(56) References Cited

OTHER PUBLICATIONS

Judgement in U.K. High Court of Justice, Case No. HP-2018-000008 dated Jul. 17, 2019 (97 pages).
Roche Opening Skeleton in U.K. High Court of Justice, Case No. HP-2018-000008 dated Jun. 7, 2019 (107 pages).
Second Expert Report of Carlolyn Bertozzi in U.K. High Court of Justice, Case No. HP-2018-000008 dated May 16, 2019 (34 pages).
Second Witness Statement of Anne Kowal in U.K. High Court of Justice, Case No. HP-2018-000008 dated APr. 10, 2019 (14 pages).
Taekda Closing Submissions in U.K. High Court of Justice, Case No. HP-2018-000008 dated Jun. 24, 2019 (158 pages).
Modern Biochemical Pharmacy, edited by Wutong Wu, China Medical Science and Technology Press, 1st edition, Jan. 2002, pp. 141-142 (with English translation).
Molecular Basis and Engineering Principles of Gene Cloning, edited by Zhiguo Liu, Shen Qu Chemical Industry Press, 1st edition, Aug. 2003, pp. 200-201 (with English translation).
Office Action dated Dec. 3, 2018 in the co-pending CN Application No. 201410108197.0 (with English translation).
Office Action dated Mar. 4, 2019 in Canadian Application No. 2,647,288.
Administrative Judgment for Chinese Application No. 201410108197.0 (2020).
Canadian Office Action dated May 19, 2021 in Canadian Patent Application No. 3,081,707.
Davies et al., "Expression of GnIII in a recombinant anti-CD20 CHO production cell line: expression of antibodies with altered glycoforms leads to an increase in ADCC through higher affinity for FcγRIII," Biotechnology and Bioengineering 74:288-294 (2001).
Israel Office Action dated Apr. 29, 2021 in IL Application No. 269201.
Kito et al., "Construction of engineered CHO strains for high-level production of recombinant proteins," Applied Microbiology and Biotechnology 60:442-448 (2002).
Canadian Office Action dated May 4, 2022 in Canadian Patent Application No. 3,081,707.
Strutzenberger, K. et al., "Changes during subclone development and ageing of human antibody-producing recombinant CHO cells," Journal of Biotechnology, 69:215-226 (1999).
Canadian Office Action dated Sep. 6, 2022 in Canadian Patent Application No. 3,128,738.
Israel Office Action dated Jul. 18, 2022 in Israel Patent Application No. 269201 (with English translation).

US 11,673,958 B2

GLYCOSYLATED ANTIBODIES

PRIORITY TO RELATED APPLICATIONS

This application is a continuation of U.S. application Ser. No. 13/298,553, filed Nov. 17, 2011, now issued as U.S. Pat. No. 8,703,919, which is a continuation of U.S. application Ser. No. 12/873,658, filed Sep. 1, 2010, now abandoned, which is a divisional of U.S. application Ser. No. 11/732,974, filed Apr. 5, 2007, now issued as U.S. Pat. No. 7,846,724, which claims the benefit of European Application Nos. 06007565.2, filed Apr. 11, 2006, and 06016203.9, filed Aug. 3, 2006, each of which applications are hereby incorporated by reference in its entirety.

The present invention relates to a recombinant antibody having an Fc region expressed and glycosylated, whereby a major core carbohydrate structure attached to the Fc region of the antibody is fully fucosylated. The present invention relates also to CHO (chinese hamster ovary) host cells, methods for selecting such CHO host cells and the use of such a recombinant antibody.

BACKGROUND OF THE INVENTION

Immunoglobulins or antibodies in their native form are usually tetrameric glycoproteins composed of two light and two heavy chains. Antibodies contain constant domains which assign the antibodies to different classes like IgA, IgD, IgE, IgM, and IgG, and several subclasses like IgG1, IgG2, IgG3, and IgG4. Antibodies of humans of class IgG1 and IgG3 usually mediate ADCC (antibody-dependent cell-mediated cytotoxicity).

There are also known other molecules which are antibody-like and contain, for example, a binding domain of a heterologous protein such as a receptor, ligand or enzyme, and the Fc region of an antibody. Such Fc fusion proteins are described, for example, by Stabila, P., et al., Nature Biotech 16 (1998) 1357-1360 and U.S. Pat. No. 5,610,297.

Monoclonal antibodies elicit four effector functions: ADCC, phagocytosis, complement-dependent cytotoxicity (CDC) and half-life/clearance rate. ADCC and phagocytosis are mediated through the interaction of cell-bound antibodies with FcγR (Fc gamma receptors); CDC through the interaction of cell-bound antibodies with a series of proteins that constitute the complement system. CDC is related to C1q binding C3 activation and/or Fc receptor binding of the Fc part. If C1q binding C3 activation and/or Fc receptor binding of an antibody constant part should be reduced, usually IgG4 antibodies are used which do not activate the complement system, do not bind C1q and do not activate C3. Alternatively, Fc parts comprising a gamma-1 heavy chain constant region with certain mutations such as L234A and L235A or D265A and N297A (WO 99/51642) are used.

It is well-known in the state of the art to modify the constant domains of antibodies for improving effector functions. Such methods are described, for example, in WO 99/54342.

Routier, F. H. et al., Glycoconjugate J. 14 (1997) 201-207 report the glycosylation pattern of a humanized IgG1 antibody expressed in CHO-DUKX cells. This antibody shows a molar ratio of Fuc: Man of 0.8:3.0, which refers to a fucosylation ratio of 80%. Niwa, R. et al., J. Immunol. Methods 306 (2005) 151-160 report for anti-CD20 IgG1 and IgG3 antibodies recombinantly produced in CHO DG44 fucosylation of 90% resp. 91%. Mimura, Y et al., J. Immunol. Methods 247 (2001) 205-216 report that butyrate increases production of human chimeric IgG in CHO-K1 cells whilst maintaining function and glycoform profile. The oligosaccharide profiles show a considerable content of afucosylated glycan structures. Raju, T. S., BioProcess International 1 (2003) 44-53 report the impact of glycosylation variation by expression systems on the biological activity of therapeutic immunoglobulins and the nomenclature. Ma, S., Anal. Chem. 71 (1999) 5185-5192 report the carbohydrate analysis of rituximab. Rituximab shows 9-10% fucosylation (Niwa, R. et al., J. Immunol. Methods 306 (2005) 151-160). Fujii, S., J. Biol. Chem. 265 (1990) 6009-6018 report that bovine IgG includes about 11% afucosylated IgG. Mizouchi, T., J. Immunol. 129 (1982) 2016-2020 report that human IgG is about 14% afucosylated. Bergwerff, A. A., Glycoconjugate J. 12 (1995) 318-330 report that antibodies produced in mouse SP2/0 contains N-glycolylneuraminic acid (NGNA) oligosaccharides in large amounts. Nahrgang, S. et al., In: Animal Cell Technology: Products from Cells, Cells as Products, Bernard, A. et al. (eds.), Kluwer Academic Publishers, Dordrecht, NL, 1999, pp. 259-261, report that for CHO expression of IgG1 after transient transfection a poor overall glycosylation is found. Lund, J. et al., Mol. Immunol. 30 (1993) 741-748 report recombinant production of a mouse-human chimeric antibody in mouse transfectoma cells. The IgG1 antibody is afucosylated in an amount of 13%. Patel, T. P. et al, Biochem. J. 285 (1992) 839-845 report on glycosylation of antibodies from hybridoma cells and mouse ascites. Niwa, R. et al., J. Immunol. Methods 306 (2005) 151-160, report for CD20 IgG1 antibody a fucosylation of 91% after recombinant production in CHO DG44 and Mori, K. et al., Biotech. Bioeng. 88 (2004) 901-908, a fucosylation of 94%. Davies, J., et al., Biotechnol. Bioeng. 74 (2001) 288-294 report that expression of antibodies with altered glycoforms leads to an increase of ADCC. Sheeley, D. M., et al., Anal. Biochem. 247 (1997) 102-110 compare antibody glycosylation in different expression systems. Shields, R. L., et al., J. Biol. Chem. 277 (2002) 26733-26740 report that lack of fucose on human IgG1 Fc improves FcγRIII binding and ADCC. Zhu, L., et al., Nature Biotechnol. 23 (2005) 1159-1169 report on the production of human antibodies in chicken eggs. WO 2004/087756 and WO 2005/005635 disclose improved antibodies against IGF-1R.

SUMMARY OF THE INVENTION

The invention comprises an antibody of human IgG1 or IgG3 type being glycosylated with a sugar chain at Asn297, said antibody being characterized in that the amount of fucose within said sugar chain is at least 99%, and in addition the amount of NGNA is 1% or less and/or the amount of N-terminal alpha-1,3-galactose is 1% or less.

According to the invention "amount" means the amount of said sugar within the sugar chain at Asn297, related to the sum of G0, G1, G2 (without mannose (4 and 5) as 100% and as calculated in example 3.

According to the invention it is possible to provide antibodies and/or CHO host cells with a fucosylation of even 99.4% or more, 99.5% or more or 99.9% or more.

Preferably the amount of NGNA is 0.5% or less, more preferably 0.1% or less and even not detectable by LCMS (Liquid Chromatography/Mass Spectrometry).

Preferably the amount of N-terminal alpha 1,3 galactose is 0.5% or less, more preferably 0.1% or less and even not detectable by LCMS.

The sugar chain show preferably the characteristics of N-linked glycans attached to Asn297 of an antibody recombinantly expressed in a CHO cell.

Preferably the antibody is a monoclonal antibody. Preferably the antibody is a chimeric, humanized or human antibody.

The invention further comprises a CHO cell capable of recombinantly expressing an antibody of human IgG1 or IgG3 type being glycosylated with a sugar chain at Asn297, said antibody being characterized in that within said sugar chain the amount of fucose is at least 99%, and in addition the amount of NGNA is 1% or less and/or the amount of N-terminal alpha 1,3 galactose is 1% or less.

Such a cell line is cell line hu MAb<IGF-1R>B1-4E10_9-16) deposited under the Budapest Treaty on the international recognition of the deposit of microorganisms for the purposes of patent procedure, with Deutsche Sammlung von Mikroorganismen und Zellkulturen GmbH (DSMZ), Germany, on Jun. 21, 2006 under Accession No. DSM ACC 2795.

Preferred sugar amounts are mentioned above.

Preferably the CHO cell is a CHO cell comprising deletion (e.g. DG44) or functional inactivation of both DHFR alleles or a deletion of one DHFR allel and a functional inactivation of the second DHFR allel (e.g. DXB11).

The invention further comprises a composition according to the invention for use in human medical therapy.

The antibody of the composition according to the invention is preferably a chimeric antibody, a human antibody, a humanized antibody, a non-human antibody, a single chain antibody comprising IgG1 or IgG3 heavy chain constant part, or a IgG1 or IgG3 heavy chain constant part.

The invention further comprises the use of an antibody according to the invention for the manufacture of a medicament. Preferably the medicament is useful for immunosuppression for the treatment of T-cell mediated disorders, autoimmune disorders, infectious diseases, cancer diseases.

The invention further comprises a pharmaceutical composition comprising an antibody according to the invention.

A further object of the invention is a method for the selection of a CHO cell for the recombinant production of a monoclonal antibody of human IgG1 or IgG3 type being glycosylated with a sugar chain at Asn297, said antibody being characterized in that the amount of fucose within said sugar chain is at least 99%, and in addition the amount of NGNA is 1% or less and/or the amount of N-terminal alpha 1,3 galactose is 1% or less, said method comprising cultivating a CHO cell, transfected with an IgG1 or IgG3 antibody and a DHFR gene, under DHFR and MTX selection pressure, picking single clones expanding the clones and selecting a clone producing an antibody with the glycosylation pattern according to the invention. Preferably cultivation is performed for at least two, preferably at least three weeks.

A further object of the invention is the use of a CHO cell according to the invention for the recombinant production of a monoclonal antibody.

A further object of the invention is a method for the recombinant production of a monoclonal antibody in a CHO cell according to the invention.

The CHO cell is a host cell useful for the recombinant expression of heterologous polypeptides.

BRIEF DESCRIPTION OF THE DRAWING

FIG. 1 is a bar chart showing the ADCC activity or lack thereof in antibodies of the invention and in control and comparative antibodies.

DETAILED DESCRIPTION OF THE INVENTION

Antibodies contain carbohydrate structures at conserved positions in the heavy chain constant regions, with each isotype possessing a distinct array of N-linked carbohydrate structures, which variably affect protein assembly, secretion or functional activity (Wright, A., and Morrison, S. L., Trends Biotechnol. 15 (1997) 26-32). The structure of the attached N-linked carbohydrate varies considerably, depending on the degree of processing, and can include high-mannose, multiply-branched as well as biantennary complex oligosaccharides (Wright, A., and Morrison, S. L., Trends Biotechnol. 15 (1997) 26-32).

Antibodies of IgG1 and IgG3 type are glycoproteins that have a conserved N-linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol Rev. 163 (1998) 59-76; Wright, A. and Morrison, S. L., Trends Biotechnol. 15 (1997) 26-32).

As used herein, the term "Fc region of human IgG type" preferably includes also naturally occurring allelic variants of the Fc region of an immunoglobulin (antibody) as well as variants having alterations which are substitutions, additions, or deletions but which do not affect Ans297 glycosylation. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U., et al., Science 247 (1990) 1306-1310).

The term "antibody" encompasses the various forms of antibodies including but not being limited to whole antibodies, antibody fragments, human antibodies, humanized antibodies and genetically engineered antibodies as long as the characteristic properties according to the invention are retained. Therefore an antibody according to the invention contains at least a functionally active (FcR binding) Fc part of IgG1 or IgG3 type comprising glycosylated Asn297.

The terms "monoclonal antibody" or "monoclonal antibody composition" as used herein refer to a preparation of antibody molecules of identical amino acid sequence. Accordingly, the term "human monoclonal antibody" refers to antibodies displaying a single binding specificity which have variable and constant regions derived from human germline immunoglobulin sequences.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Methods for producing chimeric antibodies involve conventional recombinant DNA and gene transfection techniques now well known in the art (see, e.g., Morrison, S. L., et al., Proc. Natl. Acad. Sci. USA 81 (1984) 6851-6855; U.S. Pat. Nos. 5,202,238 and 5,204,244).

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody" (see, e.g., Riechmann, L., et al., Nature 332 (1988) 323-327; and Neuberger, M. S., et al., Nature 314 (1985) 268-270). Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. Such regions are described by, e.g., Johnson, G., and Wu, T. T., Nucleic Acids Res. 28 (2000) 214-218 and the databases referenced therein and are useful as long as the properties according to the invention are retained. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g. mice) that are capable, upon immunization, of producing a full repertoire or a selection of human antibodies in the absence of endogenous immunoglobulin production. Transfer of the human germ-line immunoglobulin gene array in such germ-line mutant mice result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). A human antibody encompasses the various forms of antibodies, preferably monoclonal antibodies including but not being limited to whole antibodies, antibody fragments and genetically engineered antibodies (variant or mutant antibodies) as long as the characteristic properties according to the invention are retained. Especially preferred are recombinant human antibodies.

The term "recombinant human antibody", as used herein, is intended to include all human antibodies that are prepared, expressed, created or isolated by recombinant means, such as antibodies isolated from a host cell according to the invention, using a recombinant expression vector transfected into such a host cell.

The "constant domains" are not involved directly in binding of an antibody to an antigen, but exhibit other functions like effector functions. The heavy chain constant regions that correspond to IgG1 is called □1 chain. The heavy chain constant regions that correspond to IgG3 is called □□ chain. Human constant γ heavy chains are described in detail by Rabat, E. A. et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. Constant domains of IgG1 or IgG3 type are glycosylated at Asn297. "Asn 297" according to the invention means amino acid asparagine located at about position 297 in the Fc region; based on minor sequence variations of antibodies, Asn297 can also be located some amino acids (usually not more than ±3 amino acids) upstream or downstream. For example, in one antibody according to the invention "Asn297" is located at amino acid position 298.

Glycosylation of human IgG1 or IgG3 occurs at Asn297 as core fucosylated bianntennary complex oligosaccharide glycosylation terminated with up to 2 Gal residues. These structures are designated as G0, G1 ($\alpha$1,6 or $\alpha$1,3) or G2 glycan residues, depending from the amount of terminal Gal residues (Raju, T. S., BioProcess International 1 (2003) 44-53). CHO type glycosylation of antibody Fc parts is e.g. described by Routier, F. H., Glycoconjugate J. 14 (1997) 201-207.

The "variable region" (variable region of a light chain (VL), variable region of a heavy chain (VH)) as used herein denotes each of the pair of light and heavy chains which is involved directly in binding the antibody to the antigen.

According to the invention, an antibody producing CHO host cell can be selected which is able to provide via recombinant expression a composition of a monoclonal antibody showing a glycosylation pattern according to the invention. Such a CHO host cell comprises one or more expression vector(s) for the recombinant expression of such antibody. Preferably the host cell is stable transfected with the vector(s) and the antibody encoding nucleic acids are integrated in to the CHO host cell genome.

The term "CHO cell" encompasses the various forms of Chinese Hamster Ovary (CHO) cells based on two deleted dhfr alleles (dihydrofolate reductase deficient (dhfi$^-$)). Such dhfr$^-$ cells and methods for their generation are described e.g. in Urlaub, G. et al., Cell 33 (1983) 405-412; Urlaub, G. et al., Som. Cell Molec. Genet. 12 (1986) 555-566; Kolkekar et al., Biochemistry 36 (1997) 10901-10909. Preferably the cell is a DG44 cell line. Such CHO dhfr$^-$ cells can be produced using gamma rays to eliminate the entire dhfr locus. In non-mutated, wild-type cells, dhfr is an essential enzyme for de novo synthesis of glycine, purines, and thymidylate. This allows the dhfr gene encoded on plasmids to be used as a dominant selectable marker and a gene amplifier for the expression of proteins in dhfr$^-$ deficient cell lines. The dhfr$^-$ mutation in DG44 cells is stable and irreversible. CHO cells successfully co-transfected with expression vector(s) for an antibody of human IgG1 or IgG3 type and the DHFR gene will possess the dhfr+ phenotype and can readily be selected by culturing the colonies on media devoid of thymidine and hypoxanthine and optionally containing methotrexate (MTX) for amplification.

DG44 cells are well known in the state of the art and e.g. commercial available as cell lines e.g. from Invitrogen Corp. (USA). DG44 cells can grow adherent, in suspension and/or in serum-free medium. As used herein, the expressions "cell," "cell line," and "cell culture" are used interchangeably and all such designations of CHO dhfr$^-$ cell lines (two deleted dhfr alleles) include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the glycosylation properties according to the invention as screened for in the originally transformed cell are included.

Preferably the CHO dhfr$^-$ cell line is co-amplified with at least DHFR as one selectable marker gene. For example a mammalian expression vector containing the selectable marker(s) and the antibody gene are co-transfected into recipient CHO cells. The resulting colonies may be selected and colonies exhibiting the expected phenotype are capable of expressing the antibody. Additional selectable markers are or may not be of a dominant nature. Examples of additional selectable markers for use co-transfection include adenosine deaminase (Kaufman, R. J., et al., Proc. Natl. Acad. Sci. USA 83 (1986) 3136-3140) asparagine synthetase (Cartier, M., et al., Mol. Cell Biol. 7 (1987) 1623-1628), *E. coli* trpB gene and *Salmonella* hisD gene (Hartman, S. C., and Mulligan, R. C., Proc. Natl. Acad. Sci. USA 85 (1988) 8047-8051), M2 mouse ribonucleotide reductase (Thelander, M., and Thelander, L., EMBO J. 8 (1989) 2475-2479), human multidrug resistance gene (Kane, S. E., et al., Gene 84 (1989) 439-446), glutamine synthetase (Bebbington, C. R. et al., DNA Cloning, Vol. III, D. M. Glover (ed.), IRL Press, pp. 163-188, 1987), xanthine guanine phosphoribosyl transferase (gpt) (Mulligan, R. C., and Berg, P., Science 209 (1980) 1422-1427), hygromycin B (Santerre, R. F., et al., Gene 30 (1984) 147-156), neomycin gene (Southern, P. J., and Berg, P., J. Mol. Appl. Genet. 1 (1982) 327-341).

The selectable markers may also provide the basis upon which the genes encoding the antibody may be amplified. In co-transfection of a CHO cell line, the vector DNAs are often integrated into the chromosome of the cell at the same locus. Thus, the use of only one of the selectable markers as the basis for amplification normally results in a parallel increase in the copy number of both genes. One particular selectable marker for use in this way is dhfr which enables the desired amplification to be obtained through the use of increasing concentrations of MTX. A second preferred selectable marker is GS which allows amplification by the addition of methionine sulphoximine (MSX).

The selectable markers are of course under the control of regulatory elements of DNA so as to provide for their expression. In the case of the use of dhfr as a selectable marker, the regulatory elements are preferably of a viral source, such as from DNA tumor viruses. Particularly preferred are the use of an SV40 or adenovirus major late promoter. It is particularly advantageous in this regard to remove the enhancer element from the promoter thus effectively "crippling" it. This modification allows for increased levels of gene amplification at each concentration of methotrexate selection than would otherwise occur if a strong promoter was used. In the case of the use of neomycin as a selectable marker, an example of a suitable promoter is the mouse metallothionein promoter.

The term nucleic acid or nucleic acid molecule, as used herein, is intended to include DNA molecules and RNA molecules. A nucleic acid molecule may be single-stranded or double-stranded, but preferably is double-stranded DNA.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are cis, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in CHO host cells and the antibody is recovered from the cells or supernatant preferably after lysis).

Recombinant production of antibodies is well-known in the state of the art and described, for example, in the review articles of Makrides, S. C., Protein Expr. Purif 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in the supernant, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)).

The control sequences that are suitable for prokaryotes, for example, include a promoter, optionally an operator sequence, and a ribosome binding site. Eukaryotic cells are known to utilize promoters, enhancers and polyadenylation signals.

The monoclonal antibodies can be suitably separated from a hybridoma culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated from the hybridoma and sequenced using conventional procedures. The hybridoma cells can serve as a source of such DNA and RNA. Once identified and isolated, the DNA may be inserted into expression vectors, which are then transfected into CHO cells that do not otherwise produce immunoglobulin protein, to obtain the synthesis of recombinant monoclonal antibodies in the host cells.

In another aspect, the present invention provides a pharmaceutical composition, comprising a composition of the present invention, formulated together with a pharmaceutically acceptable carrier. Preferably a pharmaceutical composition according to WO 98/22136 is used. Such a composition contains e.g. in 1 ml 2M mg antibody, 15 mM phosphate buffer pH6.5, 30 mM sodium chloride, 25 mg mannite, arginine 10 mg, 0.1 mg Tween®20.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A "pharmaceutically acceptable salt" refers to a salt that retains the desired biological activity of the antibody and does not impart any undesired toxicological effects (see e.g. Berge, S. M., et al., J. Pharm. Sci. 66 (1977) 1-19). Such salts are included in the invention. Examples of such salts include acid addition salts and base addition salts. Acid addition salts include those derived from nontoxic inorganic acids, such as hydrochloric salts.

A composition of the present invention can be administered by a variety of methods known in the art. As will be appreciated by the skilled artisan, the route and/or mode of administration will vary depending upon the desired results.

To administer a compound of the invention by certain routes of administration, it may be necessary to coat the compound with or coadminister the compound with, a material to prevent its inactivation. For example, the compound may be administered to a subject in an appropriate carrier, for example, liposomes, or a diluent. Pharmaceutically acceptable diluents include saline and aqueous buffer solutions.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The following examples and the FIGURE are provided to aid the understanding of the present invention, the true scope of which is set forth in the appended claims. It is understood that modifications can be made in the procedures set forth without departing from the spirit of the invention.

EXAMPLES

Cell Lines

The parental cell line used for the generation of a cell line for recombinant IgG expression is a Chinese hamster ovarian (CHO) cell line, CHO-DG44 (Flintoff, W. F. et al., Somat. Cell Genet. 2 (1976) 245-261; Flintoff, W. F. et al., Mol. Cell. Biol. 2 (1982) 275-285; Urlaub, G. et al., Cell 33 (1983) 405-412; Urlaub. G. et al., Somat. Cell Mol. Genet. 12 (1986) 555-566). CHO-DG44 cells have lost both endogenous loci for the enzyme Dihydrofolate Reductase (DHFR).

CHO-DG44 cells were grown in MEM alpha Minus Medium (Gibco No. 22561), 10% dialysed FCS (Gibco No. 26400-044) and 2 mmol/L L-Glutamine, 100 µM Hypoxanthin, 16 µM Thymidin (HT supplement).

Plasmids

The expression system comprised the CMV promoter and is described in table 1. As antibody an antibody against IGF-1R (WO2005005635; AK18 or AK22) was used.

TABLE 1

| Bp | Vector element/DNA segment |
|---|---|
| 1-26 | Unique restriction sites: SgrAI, Sse83871 |
| 27-614 | Human cytomegalovirus (HCMV) promoter (CMV-Prom) including human CMV IE promoter including synthetic 5'-UTR |
| 615-641 | Linker |
| 642-780 | Murine Ig heavy chain leader sequence (L1, signal sequence intron, L2) |
| 642-686 | L1 |
| 687-768 | Signal intron (SS intron) |
| 769-780 | L2 |
| 781-1105 | Variable κ-light chain domain of IGF-1R antibody (AK18) |
| 1106-1140 | Linker |
| 1141-3134 | Human/mouse κ-light chain hybrid intron 2 |
| 2433-2913 | κ-enhancer fragment |
| 3135-3475 | Linker |
| 3476-3795 | κ-Light chain constant region (C-kappa) |
| 3796-4098 | Human Ig κ-light chain polyadenylation sequence (C-kappa pA) |
| 4099-4137 | Linker |
| 4138-5800 | Hygromycin resistance |
| 4138-4485 | SV40 promoter (SV40 Prom) incl. 72bp repeat, TATA, SV40 origin |
| 4486-4502 | Linker |
| 5403-5528 | Hygromycin-B-phosphotransferase (Hyg) |
| 5529-5535 | Linker |
| 5536-5795 | SV40 polyadenylation signal (SV40 pA) |
| 5796-5800 | Linker |
| 5801-6944 | Murine dihydrofolate reductase (DHFR) |

TABLE 1-continued

| Bp | Vector element/DNA segment |
|---|---|
| 5801-6088 | SV40 promoter (SV40 Prom) incl. 72bp repeat shortened, SV40 origin |
| 6089-6105 | Linker |
| 6106-6672 | Murine DHFR gene (murine DHFR) |
| 6673-6679 | Linker |
| 6680-6944 | SV40 polyadenylation signal (SV40 pA) |
| 6945-7181 | Linker |
| 7182-8941 | Bacterial origin of replication and selective marker derived from plasmid pUC18 |
| 7182-7792 | Origin of replication ("pUC origin") |
| 7793-7939 | Linker |
| 7940-8847 | β-Lactamase gene (Ap(r)) |
| 8848-8941 | Linker |
| 8942-9529 | Human cytomegalovirus (HCMV) promoter (CMV-Prom) including human CMV IE promoter including synthetic 5'-UTR |
| 9530-9556 | Linker |
| 9557-9696 | Murine Ig heavy chain leader sequence (L1, signal sequence intron, L2) |
| 9557-9602 | L1 |
| 9603-9685 | Signal intron (SS intron) |
| 9686-9696 | L2 |
| 9697-10051 | Variable IgG1 heavy chain domain of IGF-1R antibody (AK18) |
| 10052-10085 | Linker |
| 10086-11682 | Human/mouse heavy chain hybrid intron 2 including the part of the mouse Ig heavy chain J-segment region including the Ig heavy chain enhancer element (part $JH_3$, $JH_4$) Mouse Ig heavy chain enhancer element |
| 11683-11909 | Linker |
| 11910-13504 | Human IgG1 heavy chain constant region ($CH_1$-Hinge-$CH_2$—$CH_3$) |
| 11910-12203 | CH1 |
| 12594-12638 | Hinge |
| 12757-13086 | CH2 |
| 13184-13504 | CH3 (alternative splice site deleted) |
| 13505-13967 | Human IgG1 heavy chain polyadenylation sequence (IgG1 pA) |
| 13968-13970 | SgrAI-Linker |

Example 1

Transfection and Selection

Transfection of the expression plasmid was carried out with Fugene (Roche Diagnostics GmbH). A day after transfection, DG44 cells were put under selection pressure consisting of MEM alpha Minus Medium, 10% dialysed FCS and 2 mmol/L L-Glutamine and 20 nM Methotrexate (MTX). After 3 weeks under selection pressure, single clones were picked from the plate and expanded. Supernatants were collected and the presence of the antibody was analyzed with a human IgG-specific ELISA. Subclones were further expanded and analyzed for specific antibody production. Clones were adapted to growth in suspension culture and serum-free medium, HyQ SFM4 CHO-Utility (HyClone #SH30516) containing 20 nM MTX. In parallel, the glyco-pattern profile was determined. Subclones were selected providing defucosylation of 2.0% or lower (referring to total molar oligosaccharide amount).

Example 2

Cultivation and Purification

Cells were grown in 125 ml shake flasks (Corning) filled with 30 ml medium at 37° C., 5% CO2, 100 rpm. Cell density was measured by CASY Counter and supernatant was taken for determination of antibody concentration by protein A affinity chromatography. About 20 ml of each supernatant was purified for further biochemical characterization by Protein A chromatography (equilibration with PBS, wash with 25 mM sodiumcitrate buffer pH 5.2, elution with 100 mM sodiumcitrate buffer pH 2.8, CIP with 10 mM NaOH).)

Example 3

Analysis of Glycostructure of Antibody

Purified antibody material was analyzed by Liquid Chromatography/Mass Spectrometry (LCMS) Peptide map analysis. Samples were reduced (0.4M TRIS/HCl, 8M Guanidine/HCl, pH 8.5, DTT (3 mg/ml), carboxymethylated (iodoacetic acid) and cleaved with trypsin. The peptide glycopeptide mixture was separated with RP-HPLC and analyzed online with electrospray mass spectrometry. The m/z spectra of the glycostructure containing peptide were integrated, the results are given in Table 2.

TABLE 2

| | Relative amount of glycosylation variants | | | | |
|---|---|---|---|---|---|
| Clone No. | G0 [%] | G1 [%] | G2 [%] | NoFuc [%] | Man[1] [%] |
| 1 | 38.4 | 51.4 | 10.2 | 0.1 | 0.5 |
| 2 | 44.3 | 47.6 | 8.1 | 0.1 | 0.6 |
| 3 | 42.8 | 48.7 | 8.5 | 0.2 | 0.8 |
| 4 | 49.2 | 43.6 | 7.2 | 0.3 | 1.2 |
| 5 | 62.7 | 33.0 | 4.3 | 0.6 | 1.0 |
| 6 | 60.4 | 35.5 | 4.2 | 0.5 | 1.2 |
| 7 | 40.4 | 49.8 | 9.8 | 0.3 | 0.6 |
| 8 | 46.9 | 45.9 | 7.3 | 0.3 | 1.1 |

[1]Mannose (4 and 5) glycostructure (high mannose)

The CHO cell line clone 5 (hu MAb<IGF-1R>B1-4E10_9-16) was deposited, under the Budapest Treaty on the international recognition of the deposit of microorganisms for the purposes of patent procedure, with Deutsche Sammlung von Mikroorganismen und Zellkulturen GmbH (DSMZ), Germany, on Jun. 21, 2006 under Accession No. DSM ACC 2795.

The media used were obtained from Hyclone (HyQ SFM4 CHO-Utility, used for clone 4-6) or Sigma (C-8862, used for clone 1-3 and 7).

noFuc: amount of nonfucosylated Asn297 sugar chains
With LCMS peptide map analysis by integration of the specific ion chromatograms of all charge states for all glycopeptides.
Bisecting GlcNac, NGNA und high mannose are determined in same manor.
Bisecting GlcNac and NGNA are not detectable. Bisecting GlcNac and NGNA are not detectable, thus the amount of NGNA is 0.5% or lower, and is also 0.1% or lower. The amount of bisecting GlcNac is also 0.5% or lower, and 0.1% or lower.
An exemplary calculation of glycosylation (clone 3) is shown in table 3 (peptide comprising asn297, named H27).

TABLE 3

| | Area z = 2 | Area z = 3 | Area z = 4 | Sum | rel. amount % |
|---|---|---|---|---|---|
| H27_G0 | 616 | 198 | 0 | 814 | 28.7 |
| H27_G1 | 734 | 425 | 0 | 1158 | 40.9 |
| H27_G2 | 103 | 135 | 0 | 238 | 8.4 |
| H27_G3 | 0 | 0 | 0 | 0 | 0.0 |
| H27_G4 | 0 | 0 | 0 | 0 | 0.0 |

TABLE 3-continued

|  | Area z = 2 | Area z = 3 | Area z = 4 | Sum | rel. amount % |
|---|---|---|---|---|---|
| H27_G1_1NGNA | 0 | 0 | 0 | 0 | 0.0 |
| H27_G2_1NGNA | 0 | 0 | 0 | 0 | 0.0 |
| H27_G2_2NGNA | 0 | 0 | 0 | 0 | 0.0 |
| H27_G3_1NGNA | 0 | 0 | 0 | 0 | 0.0 |
| H27_G3_2NGNA | 0 | 0 | 0 | 0 | 0.0 |
| G0 minus GlcNAc and minus Man | 0 | 57 | 0 | 57 | 2.0 |
| G0 minus GlcNAc | 330 | 0 | 0 | 330 | 11.7 |
| G1 minus GlcNAc | 208 | 0 | 0 | 208 | 7.4 |
| Man5 | 22 | 0 | 0 | 22 | 0.8 |
| G0 minus Fuc | 5 | 0 | 0 | 5 | 0.2 |
| G1 minus Fuc | 0 | 0 | 0 | 0 | 0.0 |
| Man4 | 0 | 0 | 0 | 0 | 0.0 |
| Total |  |  |  | 2833.15 | 100.00 |
| rel. amount of glycostructures with NGNA |  |  |  |  | 0.0 |
| rel. amount of glycostructures with Galactoses (G3 and G4) |  |  |  |  | 0.0 |
| rel. amount of high mannose |  |  |  |  | 0.8 |
| Rel. amount of G0 minus Fuc and G1 minus Fuc |  |  |  |  | 0.2 |
| Sum G0 |  |  |  |  | 42.4 |
| Sum G1 |  |  |  |  | 48.2 |
| Sum G2 |  |  |  |  | 8.4 |
| Total Sum |  |  |  |  | 99.0 |
| Related to 100% G0-1-2 |  |  |  |  |  |
| G0 |  |  |  |  | 42.8 |
| G1 |  |  |  |  | 48.7 |
| G2 |  |  |  |  | 8.5 |
| Sum without Man |  |  |  |  | 99.2 |
| Sum G0/1 minus Fuc |  |  |  |  | 0.2 |
| Relative amount without Fuc |  |  |  |  | 0.2 |

Area: peak area

Relative amount without Fuc: percentage of Fuc related to all G0, G1, G2 without mannose (4 and 5) glycostructure (high mannose).

Example 4

Determination of Antibody Mediated Effector Functions by Anti-IGF-IR HuMAbs

In order to determine the capacity of the generated HuMAb antibodies to elicit immune effector mechanisms, antibody-dependent cell cytotoxicity (ADCC) studies were performed. To study the effects of the antibodies in ADCC, DU145 prostate cancer cells (1×106 in 2 to 4 ml RPMI-FM) expressing IGF-IR were labeled with 1 µl bis(acetoxymethyl) 2,2':6',2"-terpyridine-6,6"-dicarboxylate (BATDA) solution for 25 minutes at 37° C. in a cell incubator. Cells were washed four times with 10 ml of RPMI-FM and spun for 10 minutes at 200×g with brake. Afterwards, cells were adjusted to a concentrations of 1×10⁵ cells per ml. 5,000 cells were plated per well in a round bottom plate corresponding to a volume of 50 µl. HuMAb antibodies were added at a final concentration ranging from 25-0.1 ng/ml in a volume of 50 µl cell culture medium. Subsequently, 50 µl of effector cells, PBMC freshly isolated from whole blood or purified effector cells from buffycoats, were added at an E:T ratio in the range of 25:1. The plates were centrifuged immediately for 1 minute at 200×g with brake, and incubated for 2 hours at 37° C. After incubation the cells were spun down for 10 minutes at 200×g and 20 µl of supernatant were transferred to an Optiplate 96-F microtiterplate. 200 µl of Europium solution (at room temperature) were added and the mixture was incubated for 15 minutes on a shaker. Resulting fluorescence was measured in a time-resolved fluorometer using the EU-TDA protocol from Perkin Elmer.

The magnitude of cell lysis by ADCC is expressed as % of the maximum release of 2,2':6',2"-terpyridine-6,6"-dicarboxylate (TDA) from the target cells lysed by detergent corrected for spontaneous release of TDA from the respective target cells. As reference standard of an antibody showing "no ADCC" is used an antibody against KLH (keyhole limpet hemocyanin) or an IgG mixture isolated from about 35.000 donors ("Redimune"). A 75% fucose free antibody against IGF-IR was used as positive control. An antibody according to the invention showed a TDA release which is within 3×SD of the TDA release of the standard antibody (FIG. 1).

What is claimed is:

1. A human monoclonal antibody of human IgG1 type which is glycosylated with a sugar chain at Asn297, the antibody having:
   a) an amount of fucose which is at least 99% of the sugar chain;
   b) an amount of N-glycolylneuraminic acid (NGNA) which is 1% or less of the sugar chain; and
   c) an amount of N-terminal alpha-1,3-galactose which is 1% or less of the sugar chain;
   wherein the amounts of the fucose, NGNA, and N-terminal alpha-1,3-galactose are relative to the sum of the amounts of G0, G1, and G2 glycan residues, not including mannose 4 and mannose 5, which sum is 100% of the sugar chain;
   wherein the amounts are determined by Liquid Chromatography/Mass Spectrometry peptide map analysis.

2. The human antibody of claim 1, wherein the amount of NGNA is 0.5% or less.

3. The human antibody of claim 1, wherein the amount of NGNA is 0.1% or less.

4. The human antibody of claim 1, wherein the amount of N-terminal alpha-1,3-galactose is 0.5% or less.

5. The human antibody of claim 2, wherein the amount of N-terminal alpha-1,3-galactose is 0.5% or less.

6. The human antibody of claim 3, wherein the amount of N-terminal alpha-1,3-galactose is 0.5% or less.

7. The human antibody of claim 1, wherein the amount of N-terminal alpha-1,3-galactose is 0.1% or less.

8. The human antibody of claim 2, wherein the amount of N-terminal alpha-1,3-galactose is 0.1% or less.

9. The human antibody of claim 3, wherein the amount of N-terminal alpha-1,3-galactose is 0.1% or less.

10. A pharmaceutical composition comprising:
    a human monoclonal antibody of human IgG1 type which is glycosylated with a sugar chain at Asn297 and has:
    a) an amount of fucose which is at least 99% of the sugar chain;
    b) an amount of N-glycolylneuraminic acid (NGNA) which is 1% or less of the sugar chain; and
    c) an amount of N-terminal alpha-1,3-galactose which is 1% or less of the sugar chain;
    wherein the amounts of the fucose, NGNA, and N-terminal alpha-1,3-galactose are relative to the sum of the amounts of G0, G1, and G2 glycan residues, not including mannose 4 and mannose 5, which sum is 100% of the sugar chain;
    wherein the amounts are determined by Liquid Chromatography/Mass Spectrometry peptide map analysis; and
    a pharmaceutically acceptable excipient or diluent.

11. The pharmaceutical composition of claim 10, wherein the amount of NGNA is 0.5% or less.

12. The pharmaceutical composition of claim 10, wherein the amount of NGNA is 0.1% or less.

13. The pharmaceutical composition of claim 10, wherein the amount of N-terminal alpha-1,3-galactose is 0.5% or less.

14. The pharmaceutical composition of claim 11, wherein the amount of N-terminal alpha-1,3-galactose is 0.5% or less.

15. The pharmaceutical composition of claim 12, wherein the amount of N-terminal alpha-1,3-galactose is 0.5% or less.

16. The pharmaceutical composition of claim 10, wherein the amount of N-terminal alpha-1,3-galactose is 0.1% or less.

17. The pharmaceutical composition of claim 11, wherein the amount of N-terminal alpha-1,3-galactose is 0.1% or less.

18. The pharmaceutical composition of claim 12, wherein the amount of N-terminal alpha-1,3-galactose is 0.1% or less.

* * * * *